(12) United States Patent
Weisel et al.

(10) Patent No.: US 9,936,941 B2
(45) Date of Patent: Apr. 10, 2018

(54) SURGICAL INSTRUMENT FOR MANIPULATING AND PASSING SUTURE

(71) Applicant: ArthroCare Corporation, Austin, TX (US)

(72) Inventors: Thomas Weisel, Ventura, CA (US); Roger Pisarnwongs, Valencia, CA (US)

(73) Assignee: ArthroCare Corporation, Austin, TX (US)

( * ) Notice: Subject to any disclaimer, the term of this patent is extended or adjusted under 35 U.S.C. 154(b) by 822 days.

(21) Appl. No.: 13/760,163

(22) Filed: Feb. 6, 2013

(65) Prior Publication Data

US 2013/0218173 A1 Aug. 22, 2013

Related U.S. Application Data

(60) Provisional application No. 61/606,695, filed on Mar. 5, 2012, provisional application No. 61/596,160, filed on Feb. 7, 2012.

(51) Int. Cl.
*A61B 17/04* (2006.01)
*A61B 17/06* (2006.01)

(52) U.S. Cl.
CPC ...... *A61B 17/0469* (2013.01); *A61B 17/0483* (2013.01); *A61B 17/06109* (2013.01); *A61B 2017/06009* (2013.01); *A61B 2017/06042* (2013.01)

(58) Field of Classification Search
CPC ............ A61B 17/0469; A61B 17/0482; A61B 17/0483; A61B 17/0485; A61B 2017/00349; A61B 2017/06009
See application file for complete search history.

(56) References Cited

U.S. PATENT DOCUMENTS

| 292,195 | A | 1/1884 | Austin |
| 1,545,682 | A | 7/1925 | Nelson |
| 1,583,271 | A | 5/1926 | Biro |
| 1,708,578 | A | 4/1929 | Hyde |
| 2,738,790 | A | 3/1956 | Todt, Sr. et al. ............... 606/145 |
| 2,959,172 | A | 11/1960 | Held .............................. 128/340 |
| 3,630,190 | A | 12/1971 | Schmid ......................... 600/591 |
| 3,877,434 | A | 4/1975 | Ferguson et al. ............. 606/158 |

(Continued)

FOREIGN PATENT DOCUMENTS

WO 11/60446 5/2011 ............. A61B 17/04

OTHER PUBLICATIONS

UK Exam Report for GB1515504.7 dated Apr. 25, 2016, 2 pages.
UK Exam Report for GB1415673.1 dated Apr. 12, 2016, 3 pages.

*Primary Examiner* — Sarah W Aleman
(74) *Attorney, Agent, or Firm* — Norman F. Hainer, Jr.

(57) ABSTRACT

A suture manipulating instrument for passing and retrieving suture through a tissue includes a handle mechanism, an elongate shaft extending from the handle, and a working distal end. The working distal end includes a needle body, a lumen defined by the needle body, a tissue penetrating distal tip, and a lateral slot. A preformed inner member is movably disposed within the lumen of the needle. The handle mechanism is used to extend the wire from the lateral slot of the needle, and to retract the wire into the lateral slot, allowing the working end of the instrument to grasp and manipulate suture by pinning and/or trapping the suture against the needle.

30 Claims, 31 Drawing Sheets

(56) References Cited

U.S. PATENT DOCUMENTS

| | | | |
|---|---|---|---|
| 4,002,169 A | 1/1977 | Cupler, II | 604/22 |
| 4,230,123 A | 10/1980 | Hawkins, Jr. | 600/435 |
| 4,372,302 A | 2/1983 | Akerlund | 128/840 |
| 4,378,019 A | 3/1983 | Yamada | 606/187 |
| 4,641,652 A | 2/1987 | Hutterer et al. | 606/148 |
| 4,779,616 A | 10/1988 | Johnson | 606/148 |
| 4,781,190 A | 11/1988 | Lee | 606/139 |
| 4,796,626 A | 1/1989 | Devries | 606/148 |
| 4,816,656 A | 3/1989 | Nakano et al. | 235/380 |
| 4,935,008 A | 6/1990 | Lewis, Jr. | 604/510 |
| 5,015,250 A | 5/1991 | Foster | 606/147 |
| 5,106,369 A | 4/1992 | Christmas | 604/506 |
| 5,127,916 A * | 7/1992 | Spencer | A61B 19/54 606/185 |
| 5,149,329 A | 9/1992 | Richardson | 604/272 |
| 5,172,701 A | 12/1992 | Leigh | 600/566 |
| 5,176,700 A | 1/1993 | Brown et al. | 606/206 |
| 5,181,919 A | 1/1993 | Bergman et al. | 606/144 |
| 5,201,741 A | 4/1993 | Dulebohn | 606/113 |
| 5,217,024 A | 6/1993 | Dorsey et al. | 600/571 |
| 5,222,508 A | 6/1993 | Saitta | 128/898 |
| 5,222,977 A | 6/1993 | Esser | 606/223 |
| 5,242,456 A | 9/1993 | Nash et al. | 606/142 |
| 5,250,054 A | 10/1993 | Li et al. | 606/148 |
| 5,250,055 A | 10/1993 | Moore et al. | 606/148 |
| 5,261,917 A | 11/1993 | Hasson et al. | 606/139 |
| 5,281,237 A | 1/1994 | Gimpelson | 606/144 |
| 5,312,422 A | 5/1994 | Trott | 606/144 |
| 5,364,410 A | 11/1994 | Failla et al. | 606/148 |
| 5,385,568 A | 1/1995 | Boebel | |
| 5,387,227 A | 2/1995 | Grice et al. | 606/222 |
| 5,405,354 A | 4/1995 | Sarrett | 606/148 |
| 5,499,991 A * | 3/1996 | Garman | A61B 17/0483 606/148 |
| 5,501,692 A | 3/1996 | Riza | |
| 5,573,542 A | 11/1996 | Stevens | 606/144 |
| 5,618,290 A | 4/1997 | Toy et al. | 606/139 |
| 5,643,292 A | 7/1997 | Hart | |
| 5,653,716 A | 8/1997 | Malo et al. | 606/139 |
| 5,658,299 A * | 8/1997 | Hart | A61B 17/12013 606/139 |
| 5,817,111 A * | 10/1998 | Riza | A61B 17/0483 112/169 |
| 5,910,148 A | 6/1999 | Wenstrom, Jr. | |
| 6,016,905 A | 1/2000 | Kendrioski | |
| 6,022,360 A | 2/2000 | Reimels et al. | 606/144 |
| 6,183,482 B1 | 2/2001 | Bates | |
| 6,221,083 B1 | 4/2001 | Mayer | 606/139 |
| 6,245,079 B1 | 6/2001 | Nobles et al. | 606/144 |
| 6,440,144 B1 | 8/2002 | Bacher | 606/142 |
| 6,454,702 B1 | 9/2002 | Smith | 600/104 |
| 6,503,264 B1 | 1/2003 | Birk | 606/191 |
| 6,510,077 B1 | 1/2003 | Alvandpour et al. | 365/154 |
| 6,517,539 B1 | 2/2003 | Smith | 606/47 |
| 6,517,552 B1 | 2/2003 | Nord et al. | 606/144 |
| 6,537,205 B1 | 3/2003 | Smith | 600/104 |
| 6,551,331 B2 | 4/2003 | Nobles et al. | 606/144 |
| 6,562,052 B2 | 5/2003 | Nobles et al. | 606/144 |
| 6,610,072 B1 | 8/2003 | Christy et al. | 606/148 |
| 6,629,984 B1 | 10/2003 | Chan | 606/148 |
| 6,761,717 B2 | 7/2004 | Bales et al. | 606/47 |
| 6,770,084 B1 | 8/2004 | Bain et al. | 606/144 |
| 6,840,900 B2 | 1/2005 | Smith | 600/104 |
| 6,881,186 B2 | 4/2005 | Smith | 600/104 |
| 6,911,034 B2 | 6/2005 | Nobles et al. | 606/144 |
| 6,972,017 B2 | 12/2005 | Smith | 606/47 |
| 6,979,338 B1 | 12/2005 | Loshakove et al. | 606/153 |
| 6,984,237 B2 | 1/2006 | Hatch et al. | 606/144 |
| 7,004,952 B2 | 2/2006 | Nobles et al. | 606/144 |
| 7,022,131 B1 | 4/2006 | Derowe et al. | 623/1.11 |
| 7,033,315 B2 | 4/2006 | Smith | 600/104 |
| 7,052,495 B2 | 5/2006 | Smith | 606/47 |
| 7,063,711 B1 | 6/2006 | Loshakove et al. | 606/153 |
| 7,090,686 B2 | 8/2006 | Nobles et al. | 606/144 |
| 7,094,248 B2 | 8/2006 | Bachinski et al. | 606/153 |
| 7,112,208 B2 | 9/2006 | Morris et al. | 606/144 |
| 7,276,067 B2 | 10/2007 | Bales et al. | 606/47 |
| 7,341,564 B2 | 3/2008 | Zwiefel et al. | 600/564 |
| 7,361,180 B2 | 4/2008 | Saadat | 606/139 |
| 7,377,927 B2 | 5/2008 | Burdulis, Jr. et al. | 606/148 |
| 7,544,199 B2 | 6/2009 | Bain et al. | 606/144 |
| 7,571,729 B2 | 8/2009 | Saadat | 128/898 |
| 7,618,426 B2 | 11/2009 | Ewers et al. | 606/139 |
| 7,621,925 B2 | 11/2009 | Saadat et al. | 606/139 |
| 7,625,386 B2 | 12/2009 | Abe et al. | 606/144 |
| 7,632,308 B2 | 12/2009 | Loulmet | 623/2.1 |
| 7,637,918 B2 | 12/2009 | Dant | 606/144 |
| 7,704,264 B2 | 4/2010 | Ewers et al. | 606/151 |
| 7,736,374 B2 | 6/2010 | Vaughan et al. | 606/153 |
| 7,744,613 B2 | 6/2010 | Ewers et al. | 606/153 |
| 7,758,597 B1 | 7/2010 | Tran et al. | 606/144 |
| 7,803,167 B2 | 9/2010 | Nobles et al. | 606/144 |
| 7,824,326 B2 | 11/2010 | Wagner et al. | 600/37 |
| 7,842,046 B1 | 11/2010 | Nakao | 606/144 |
| 7,850,705 B2 | 12/2010 | Bachinski et al. | 606/153 |
| 7,867,164 B2 | 1/2011 | Butler et al. | 606/208 |
| 7,879,048 B2 | 2/2011 | Bain et al. | 606/144 |
| 7,883,519 B2 | 2/2011 | Oren et al. | 606/148 |
| 7,918,783 B2 | 4/2011 | Maseda et al. | 600/104 |
| 7,918,845 B2 | 4/2011 | Saadat et al. | 606/1 |
| 7,918,868 B2 | 4/2011 | Marshall et al. | 606/144 |
| 7,918,869 B2 | 4/2011 | Saadat et al. | 606/153 |
| 7,927,342 B2 | 4/2011 | Rioux | 606/148 |
| 7,942,898 B2 | 5/2011 | Ewers et al. | 606/222 |
| 7,951,157 B2 | 5/2011 | Gambale | 606/144 |
| 7,955,340 B2 | 6/2011 | Michlitsch et al. | 606/139 |
| 7,963,972 B2 | 6/2011 | Foerster et al. | 606/139 |
| 7,976,539 B2 | 7/2011 | Hlavka et al. | 606/27 |
| 8,033,983 B2 | 10/2011 | Chu et al. | 600/37 |
| 8,062,295 B2 | 11/2011 | McDevitt et al. | 606/60 |
| 8,066,719 B2 | 11/2011 | Ewers et al. | 606/139 |
| 8,075,574 B2 | 12/2011 | May et al. | 606/148 |
| 8,088,131 B2 | 1/2012 | Watschke et al. | 606/144 |
| 8,105,343 B2 | 1/2012 | White et al. | 606/144 |
| 8,109,966 B2 | 2/2012 | Ritchart et al. | 606/232 |
| 8,123,671 B2 | 2/2012 | Evans et al. | 600/30 |
| 8,133,258 B2 | 3/2012 | Foerster et al. | 606/232 |
| 8,137,381 B2 | 3/2012 | Foerster et al. | 606/232 |
| 8,177,796 B2 | 5/2012 | Akyuz et al. | 606/144 |
| 8,252,005 B2 | 8/2012 | Findlay, III et al. | 606/139 |
| 8,556,916 B2 * | 10/2013 | Torrie | A61B 17/0469 606/148 |
| 2001/0018592 A1* | 8/2001 | Schaller | A61B 17/0469 606/151 |
| 2004/0249394 A1 | 12/2004 | Morris et al. | 606/144 |
| 2005/0070922 A1 | 3/2005 | Field et al. | 606/139 |
| 2005/0228407 A1 | 10/2005 | Nobles et al. | 606/144 |
| 2005/0228426 A1 | 10/2005 | Campbell | 606/192 |
| 2005/0234479 A1 | 10/2005 | Hatch et al. | 606/144 |
| 2007/0038230 A1* | 2/2007 | Stone | A61B 17/0482 606/139 |
| 2007/0118152 A1 | 5/2007 | Page | 606/148 |
| 2007/0198032 A1 | 8/2007 | Ortiz | |
| 2008/0027468 A1 | 1/2008 | Fenton, Jr. et al. | 606/144 |
| 2008/0077162 A1 | 3/2008 | Domingo | 606/146 |
| 2009/0082787 A1 | 3/2009 | Pang | |
| 2010/0057109 A1 | 3/2010 | Clerc et al. | 606/144 |
| 2010/0087838 A1 | 4/2010 | Nobles et al. | 606/144 |
| 2010/0130990 A1 | 5/2010 | Saliman | 606/145 |
| 2010/0256657 A1 | 10/2010 | Domingo | 606/145 |
| 2010/0318139 A1 | 12/2010 | Beauchamp | 606/86 R |
| 2011/0029000 A1 | 2/2011 | Lavi et al. | 606/148 |
| 2011/0066165 A1 | 3/2011 | Skinlo et al. | 606/145 |
| 2011/0106124 A1 | 5/2011 | Beauchamp | 606/170 |
| 2011/0152891 A1 | 6/2011 | McLawhorn et al. | 606/145 |
| 2011/0251626 A1 | 10/2011 | Wyman et al. | 606/144 |
| 2011/0270280 A1 | 11/2011 | Saliman | 606/145 |
| 2012/0004647 A1 | 1/2012 | Cowley | |
| 2012/0016384 A1 | 1/2012 | Wilke et al. | 606/144 |
| 2012/0053622 A1 | 3/2012 | Schulman | 606/232 |
| 2012/0123448 A1 | 5/2012 | Pamichev | |
| 2012/0209300 A1 | 8/2012 | Torrie | |

(56) References Cited

U.S. PATENT DOCUMENTS

2013/0139829 A1 6/2013 Rutan
2014/0188137 A1 7/2014 Piccirillo

\* cited by examiner

FIG. 27a
FIG. 27b

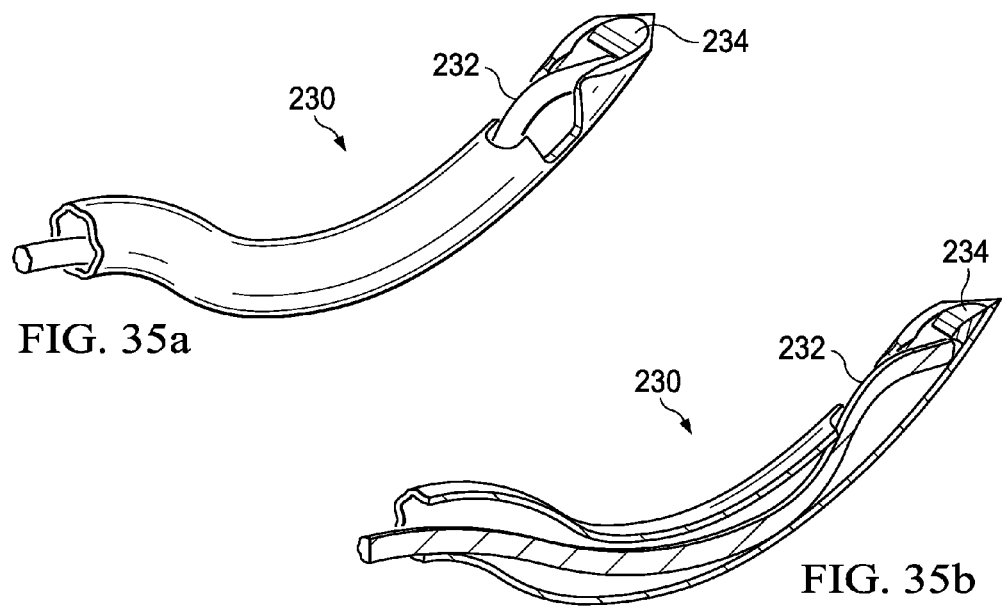
FIG. 35a
FIG. 35b
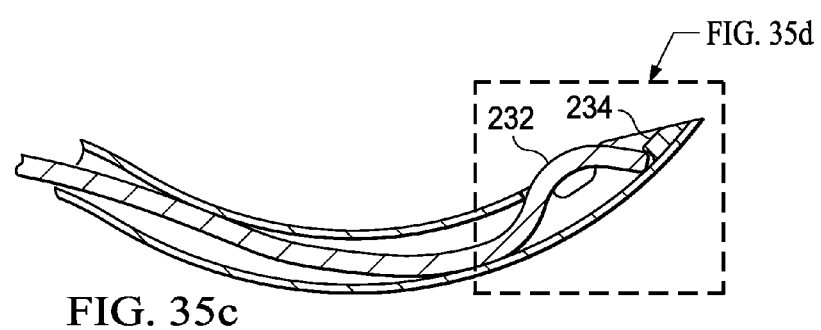
FIG. 35c
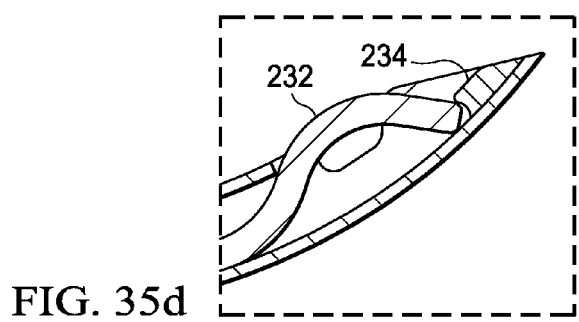
FIG. 35d

SURGICAL INSTRUMENT FOR MANIPULATING AND PASSING SUTURE

CROSS REFERENCE TO RELATED APPLICATION

This application claims priority to provisional application No. 61/596,160, filed Feb. 7, 2012, entitled "Instrument To Manipulate and Pass Suture" and provisional application No. 61/606,695 filed Mar. 5, 2012, entitled "Instrument To Manipulate and Pass Suture" each of which the entirety is incorporated by reference herein.

FIELD OF THE INVENTION

The present invention relates to a surgical instrument that can manipulate and pass suture through tissue.

BACKGROUND

Endoscopic surgery involves the performance of surgical procedures through small openings and under visualization using an endoscope. Access to a target tissue is normally provided through one or more portals formed directly in the patient's body or through one or more cannulas inserted into the patient's body through small incisions. A desired surgical procedure is carried out by a surgeon through the use of elongated instruments inserted through these cannulas.

Often it is necessary to pass suture through tissue during an endoscopic procedure. This could be required to mend a tear in the tissue or to connect two or more pieces of the soft tissue to one another. Although this task is not uncommon, passing and retrieving suture through tissue can be challenging in an endoscopic or arthroscopic procedure where visualization and space is limited.

Various endoscopic instruments have been developed to pass and retrieve suture through tissue. In some instances, retrieval of suture is accomplished by simply grasping it with regular forceps or other graspers having a suture capturing aperture formed at the distal tip when the forceps jaws are closed. Some suture retrievers include simple loops which extend from the tip of an elongated tube and which can be closed upon a suture passed through the loop.

U.S. Pat. No. 5,250,054 to Li, for example, discloses a suture retriever in the form of a knot tying device having an elongated inner rod slidably situated within an elongated outer sleeve. The distal end of the inner rod is provided with a pre-formed bend and the tip has a crochet-type hook to retrieve suture. This device, however, requires a separate needle to suture tissue.

Other devices combine a needle and suture grasper in one instrument. For example, U.S. Pat. No. 5,312,432 to Trott describes an endoscopic suturing needle having an elongated tubular housing having a needle at the distal tip and a trigger mechanism to advance and retract the needle relative to the housing. The needle is pointed and flat and has a recess provided at a predetermined distance proximal to the needle tip. The recess provides an opening to capture suture material therein. This allows the needle to either push or pull suture through selected tissue. Repeated manipulation of the suture can thus create the desired surgical stitch.

Another type of suturing needle is disclosed in U.S. Pat. No. 5,222,977 to Esser in which the needle tip is stationary and a movable slide is provided to open and close a suture receiving recess spaced a predetermined distance from the needle tip.

Many of the above referenced devices are limited because the suture needle/retrieval devices have suture snares which are situated on or in line with the needle body. Consequently, the device must be manipulated close enough to the suture to guide the suture into a suture receiving recess so the recess can be closed to retain the suture. In an endoscopic procedure positioning the suture in such close proximity to the recess can be difficult.

U.S. Pat. No. 8,066,718 to Weisel et al. discloses an expandable needle suture apparatus comprising bifurcated needle portions which define a suture slot.

U.S. Pat. No. 5,499,991 to Garman discloses a suture retriever and method for manipulating suture during endoscopic surgical procedures. The suture retriever has an elongated housing provided with a solid needle tip and a lateral opening situated proximal the needle tip. A suture engaging hook is extendable through the lateral opening and away from the axis of the housing in order to snare a suture. The hook is situated at the distal end of an elongated flexible support which is pre-formed in order to enable the hook to be laterally displaced from the axis of the needle tip when the support is moved distally relative to the lateral opening. When a suture is engaged by the hook, the latter is retracted proximally in order to place and hold the suture adjacent the lateral opening.

A problem with hooks or the like, however, is that hooks or similar grasping features tend to increase the size of the device profile penetrating the tissue, making endoscopic surgical procedures more challenging. Adding hinged jaw mechanisms make it harder to work in the tight needle bends required to reach certain anatomical areas such as the inferior labrum. Adding a hook at the distal end also increases the probability of inadvertently snaring tissue, which may damage the tissue and/or the device.

Suturing the labrum, for example, can prove challenging particularly when the tissue is severely damaged and only small areas of tissue are available to pass suture. In such cases, a novel device would be desired that could decrease the overall profile of the feature penetrating the tissue, and optimize the working profile of the instrument to improve access to the working site.

Another shortcoming with various suturing devices is that they are relatively complex to operate, making it harder for the average surgeon to utilize, and increasing the likelihood of device failure.

Accordingly, an endoscopic suturing instrument for manipulating suture through tissue which overcomes the above described shortcomings is still desirable.

SUMMARY OF THE INVENTION

A suture manipulating instrument passes suture through tissue. The instrument comprises a handle mechanism and a working distal end. The working distal end comprises a needle and a preformed inner member extending therethrough. The handle mechanism can be used to manipulate the needle and wire in a manner which would allow the wire to grasp and manipulate suture by pinning and/or trapping the suture against the needle.

In an embodiment a suture instrument for manipulating and passing suture through a tissue comprises a handle; an elongate tubular shaft extending from the handle, and a needle extending from the distal section of the tubular shaft. The needle comprises an outer body defining a lumen extending therethrough, a tissue penetrating distal tip, and a laterally disposed slot along the body and in communication with said lumen.

In embodiments the slot may extend along the body of the needle from a first location proximal the distal tip to the distal tip. In embodiments, the distal tip may be hollow beveled structure.

In embodiments the instrument may further comprise an elongate inner member such as but not limited to a wire member. The elongate inner member is movably disposed within the lumen of the needle. The inner member moves from a retracted configuration in which at least a portion of the distal section of the inner member is situated within the slot of the needle, and an extended configuration in which the distal section of the inner member extends from the slot of the needle. The distal section of the inner member preferably has a preformed shape which the distal section assumes when the inner member is in the extended configuration and the distal section is unconstrained by the lumen of the needle and wherein the preformed shape comprises a first bend which directs the distal section of the inner member at a first angle laterally away from a needle axis. The distal section of the inner member and the slot of the needle cooperate together to clamp a suture disposed therebetween when the inner member is in the retracted configuration.

The structure of the inner member may vary widely. In one embodiment, the inner member is branchless. In another embodiment the preformed shape of the distal section of the inner member is hook-less.

The diameter of the inner diameter may be constant or vary along the length. The inner member may comprise one or more bends along its length. In one embodiment the first bend assumes a first angle of at least 45 degrees with respect to the needle axis when the inner member is unconstrained.

In another embodiment the inner member comprises a discrete second bend distal to the first bend. The second bend directs a length of the distal section of the inner member at a second angle with the needle axis, and the second angle being less than the first angle.

In another embodiment the inner wire member comprises a discrete third bend distal to the second bend.

The shape of the needle may also vary. In one embodiment the body of the needle comprises a side wall, and a suture holding section in the side wall for locating the suture when clamped between the needle and the inner member. The suture holding section may comprise a recess in the side wall.

In embodiments the recess comprises a distal surface, a base, and a proximal surface which, when the inner member is in the retracted configuration, collectively hold the suture therebetween.

In one embodiment the distal surface forms a distal ramp and the distal ramp forms an angle between 20 and 65 degrees with the needle axis.

In embodiments the base of the suture holding section has a length greater than 0.3 mm. In one embodiment the recess has a depth greater than 0.3 mm.

In embodiments the proximal surface forms a proximal ramp and the proximal ramp forms an angle greater than 90 degrees with the needle axis.

In another embodiment the suture holding section comprises an undercut in at least one of the proximal and distal surfaces.

In another embodiment the slot further comprises a wire relief section proximal the suture holding section.

In another embodiment the inner member comprises a wire bundle.

In another embodiment the inner member comprises a trapping feature, and the trapping feature is one selected from the group consisting of a hold, ferrel, cleat, clamp, wedge, and bulb.

In another embodiment the suture instrument comprises a lever movably disposed in said handle and linked to the inner member to manipulate the inner member from the retracted configuration to the extended configuration.

In another embodiment the shape of the distal section of the needle is curved. In one embodiment the shape of the distal section of the needle is crescent shaped.

In another embodiment the distal tip of the needle comprises an open cavity for receiving a tip section of the inner member when the inner member is refracted.

In another embodiment a suture instrument for manipulating and passing suture through a tissue comprises: a handle; an elongate tubular shaft extending from the handle; and a needle extending from the distal section of the tubular shaft. The needle comprises an outer body defining a lumen extending therethrough, a tissue penetrating distal tip, and a slot along the body and in communication with said lumen; and an elongate inner member movably disposed within said lumen of said needle. The inner member and needle cooperate together to move between a plurality of configurations including: i) a closed configuration in which at least a portion of the distal section of the inner member is situated within the slot of the needle to clamp the suture therebetween; ii) an open configuration in which the distal section of the inner member extends from the slot of the needle and defines a suture capture zone between the inner member and the needle; and iii) an intermediate configuration in which the inner member and the needle loosely encircle a section of suture such that the suture is slidably held therebetween.

In another embodiment the distal section of the inner member has a hook-less preformed shape which the inner member assumes when the inner member is in the open configuration.

In another embodiment the inner member preformed shape comprises a plurality of discrete bends.

In another embodiment the needle comprises a crescent shape.

In another embodiment the slot comprises a plurality of sections, and said plurality of sections include a proximally disposed wire relief section, and a suture holding section distal to the wire relief section.

In another embodiment a method of endoscopically manipulating and passing suture through tissue comprises the steps of: piercing the tissue at a first location with a needle to place the needle in proximity to the suture to be retrieved; extending an elongate inner member from a lateral slot in the needle thereby creating a suture capture zone between the inner member and the needle; positioning the suture capture zone around the suture; manipulating a distal tip section of the inner member into the lateral slot of the needle while the suture is within the suture capture zone, thereby clamping the suture between the inner member and the needle such that said suture is compressed between the inner member and the needle; and removing said needle from the tissue to retrieve the suture through the tissue.

In another embodiment the clamping step is carried out by retracting the inner member through the needle.

In another embodiment the method further comprises piercing the tissue at a second location with the needle while the needle is carrying the suture to place the suture through the tissue, said step of piercing the tissue at a second location being performed prior to the step of piercing the tissue at a first location. The method further comprising extending the elongate inner member from the lumen in the needle thereby unclamping the suture from the inner member and the needle; and removing said needle from said tissue, thereby leaving the suture extending through said tissue.

In another embodiment the extending step is performed by extending a distal tip of the inner member in a first direction making a first angle with a needle axis of the needle and a second direction making a second angle with the needle axis, and wherein the second angle is less than the first angle.

In another embodiment the inner member is a preformed wire and comprises a plurality of discrete bends.

In another embodiment the tissue to be sutured is a shoulder labrum.

BRIEF DESCRIPTION OF THE DRAWINGS

FIGS. 27a-27b are perspective and side views respectively of the working end of another suture manipulating instrument in an extended configuration;

FIGS. 34b-34c are various cross sectional views of the needle distal section and inner member shown in FIG. 34a;

FIG. 35a is a perspective view of the working end of another needle distal section and inner member shown in a retracted configuration;

FIGS. 35b-35c are various cross sectional views of the needle distal section and inner member shown in FIG. 35a;

FIG. 35d is an enlarged view of a distal portion of the needle and inner shown in FIG. 35c;

FIGS. 36b-36c are various cross sectional views of the needle distal section and inner member shown in FIG. 36a.

DETAILED DESCRIPTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

Figure 1:
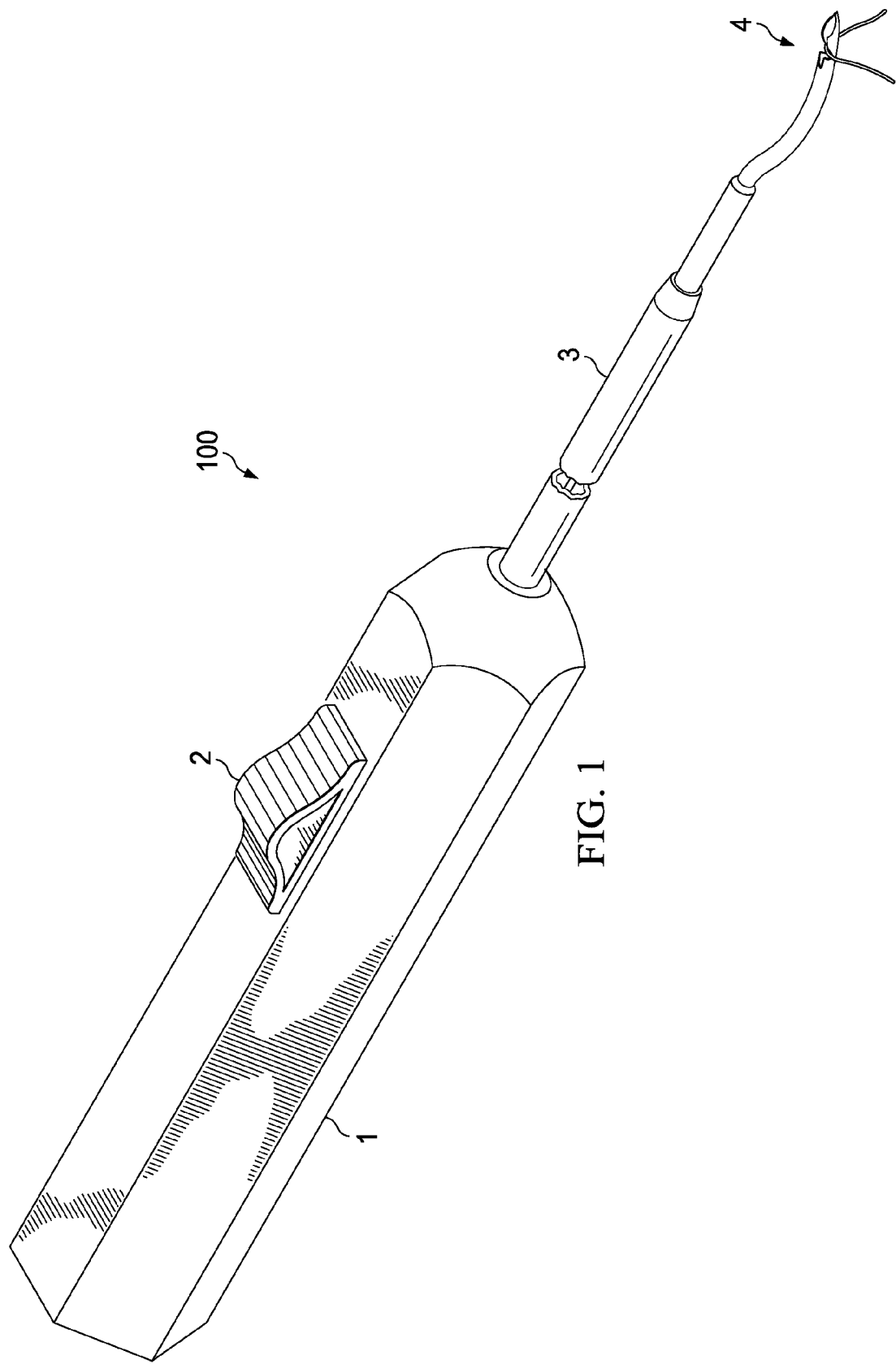
FIG. 1 is a perspective view of a suture manipulating instrument holding a suture.

A surgical instrument 100 for manipulating and passing suture is shown in FIG. 1. The instrument 100 comprises a handle 1, a lever, slide, or button 2, an elongate shaft 3, and a working end 4. Slide 2 controls the suturing manipulating mechanism at the working end 4, as will described herein.

The instrument may be used to pass and/or retrieve suture through tissue in a wide variety of applications including, for example, labrum or rotator cuff repair.

Figure 2:
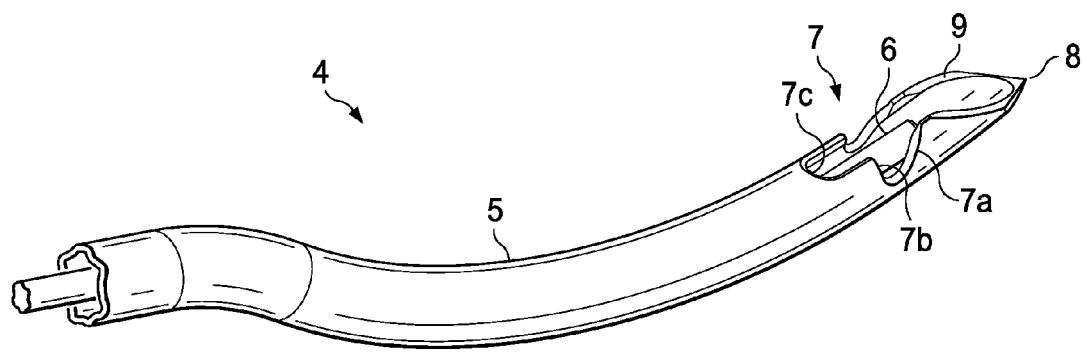
FIGS. 2-3 are perspective and cross sectional views respectively of the working end of a suture manipulating instrument in a retracted configuration.
Figure 3:
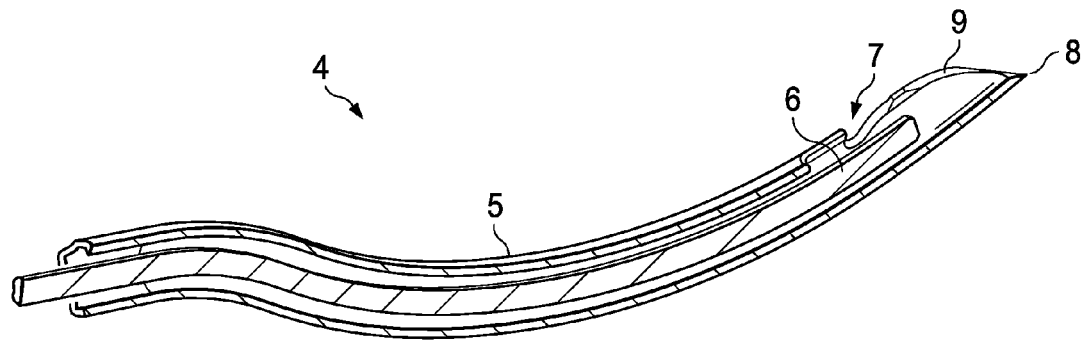

A detailed view of one possible configuration of the working end 4 is shown in FIGS. 2 and 3. The working end 4 is shown having a needle 5 and an inner member 6 (shown in a retracted state). The needle 5 has a laterally disposed suture slot 7 and a needle point or tissue penetrating distal tip 8. Needle point 8 may be formed variously, such as for example, a bevel 9 as shown in FIG. 2.

The suture slot 7 is preferably configured in such a manner to facilitate suture grasping when suture is pinned or clamped between the inner member 6 and the walls of the needle 5.

In the configuration shown in FIGS. 2-3, the suture slot 7 has a distal ramp 7a, a vertical wall 7b, and a wire relief slot 7c. As discussed herein, features 7a and 7b can have different configurations of vertical and/or ramp walls. Additionally, the needle point 8 can be used to facilitate tissue puncturing.

Figure 4:
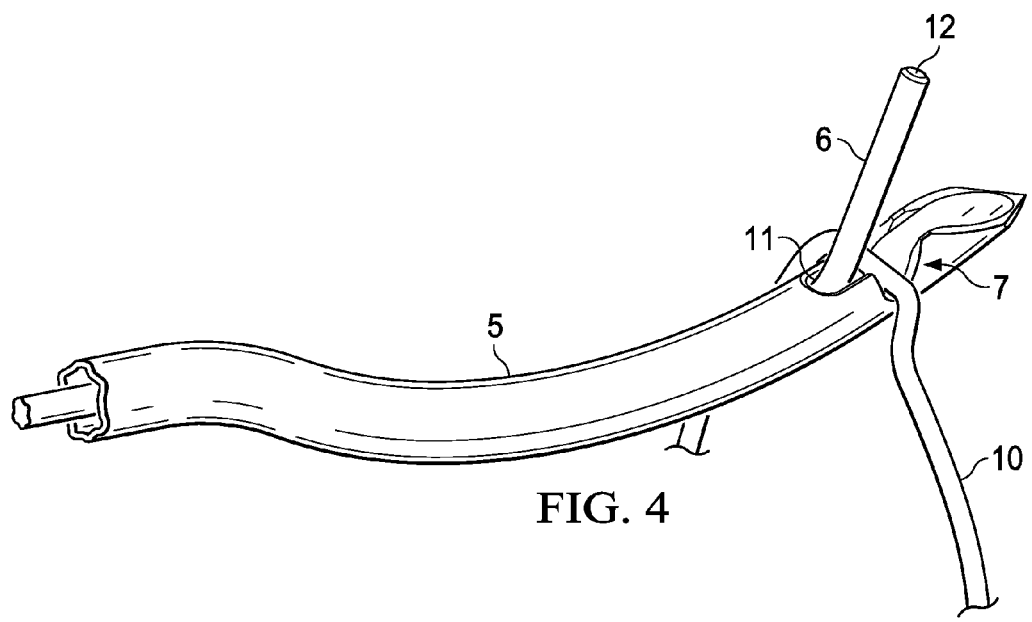
FIGS. 4-5 are perspective and cross sectional views respectively of the working end of a suture manipulating instrument in an extended configuration.
Figure 5:
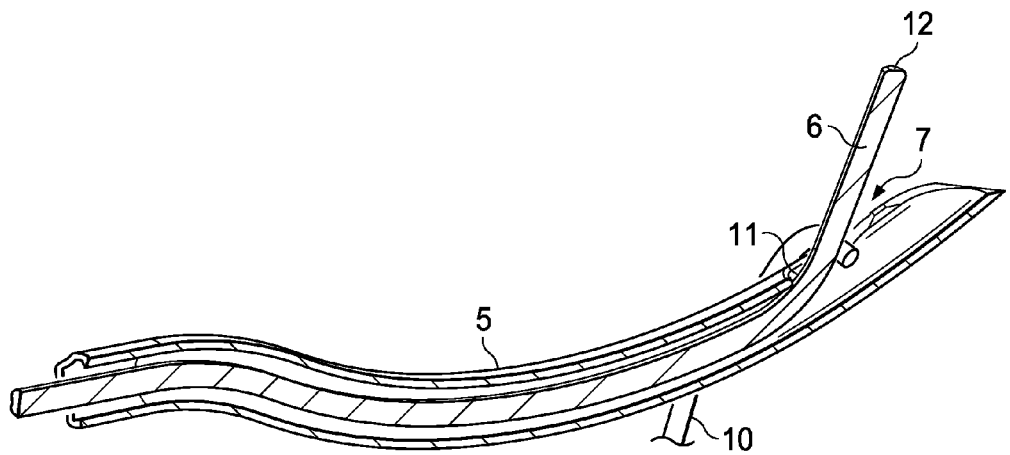

FIGS. 4 and 5 show inner member 6 in an extended or deployed state with a suture 10 lying within the suture slot 7 of needle 5. In the embodiment shown, a single proximal bend 11 is preformed in the inner member 6 proximal to the inner member tip 12.

The inner member may be formed in such a manner that causes its tip 12 to move away from the needle 5 as the inner member 6 is deployed. This action creates space (e.g., a suture capture zone) between the inner member 6 and needle 5 to allow the suture 10 to slide in between said inner member 6 and needle 5. Inner member is shown in this embodiment as a wire member. However, the inner member may be fabricated from other materials and take other forms. For example, inner member may be a metal or alloy filament, braid, or wire bundle comprising one or more elements. A preferred material is super elastic materials such as Nitinol.

The inner wire 6 is retracted once the suture 10 is properly positioned between the inner wire 6 and needle 5. Interaction between the proximal bend 11 on inner wire 6 and the suture slot 7 results in the inner wire tip 12 being displaced toward the needle axis and subsequently traps the suture 10.

Figure 6:
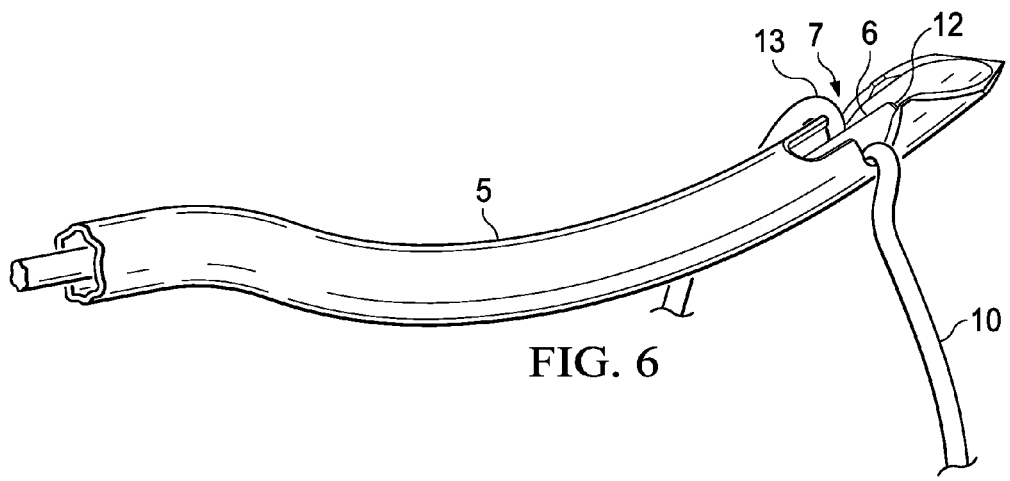
FIGS. 6-7 are perspective and cross sectional views respectively of the working end of a suture manipulating instrument in a suture grasping configuration.
Figure 7:
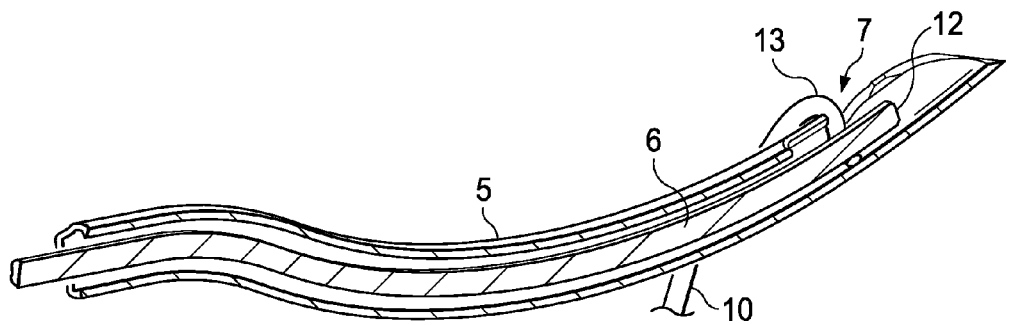

FIGS. 6 and 7 show the inner wire 6 in the retracted state with a suture 10 clamped or pinned across the suture slot 7. In this embodiment the suture 10 is forced into a circuitous or tortuous path 13 between the inner wire 6 and the suture slot 7 which increases the hold on the suture 10.

Procedure

Figure 8:
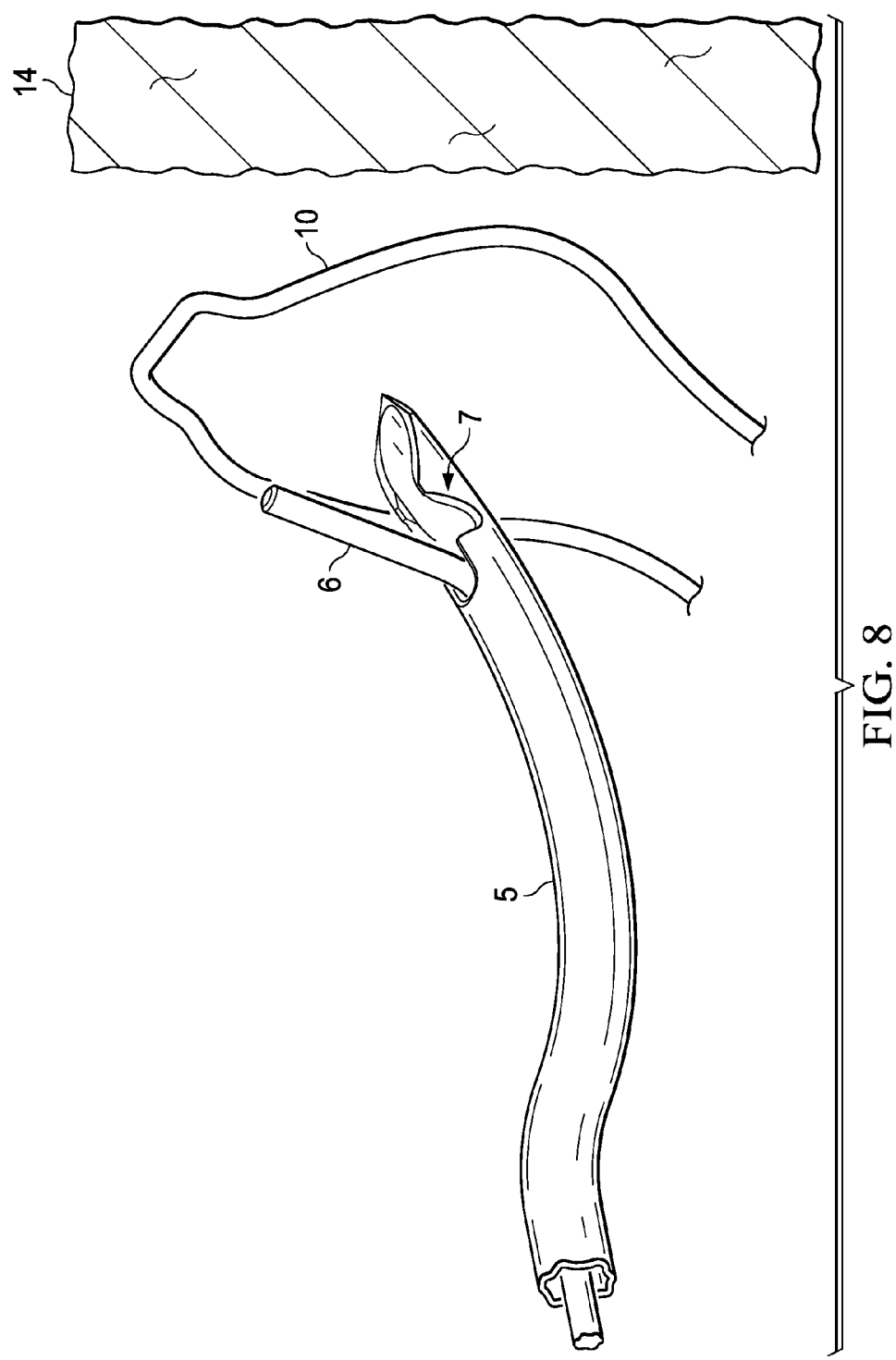
FIGS. 8-18 are illustrations of a surgical instrument manipulating and passing suture through tissue.

FIGS. 8 to 13 show one possible method of using the current embodiment to pass suture from one side of tissue 14 to the other. Examples of tissue include without limitation labral tissue. FIG. 8 shows the instrument with the inner member 6 in the extended or deployed state and in position to grab suture.

Figure 9:
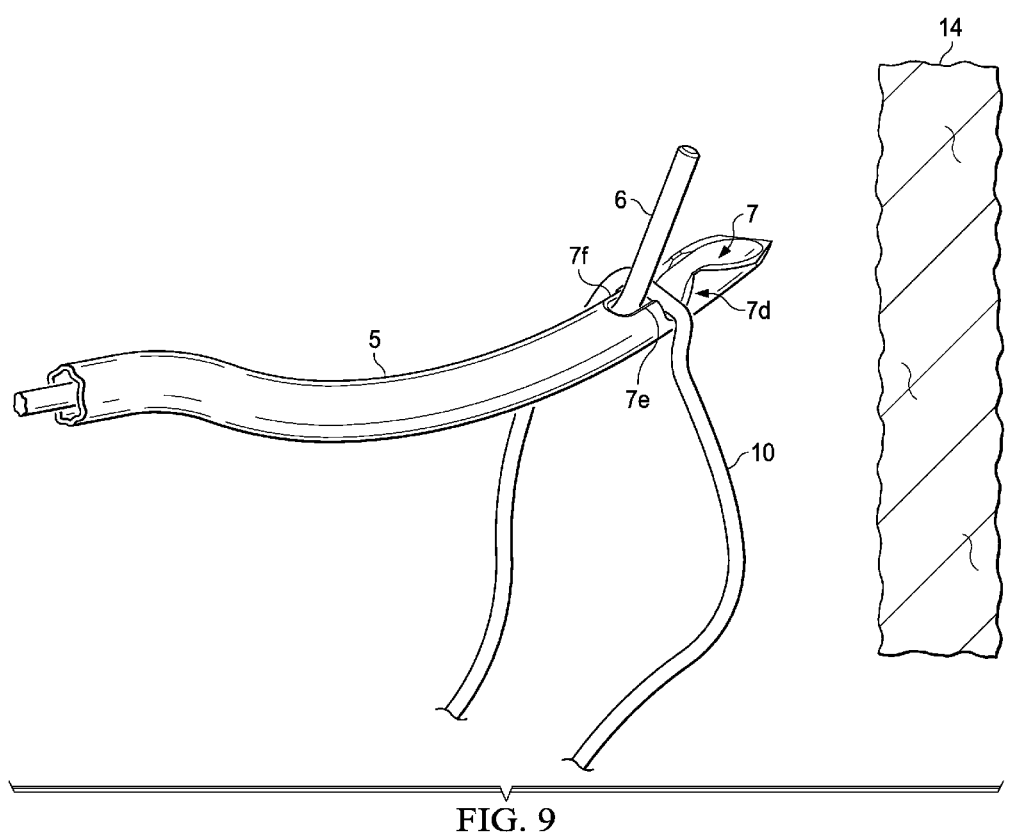

The device is then manipulated to position the suture 10 between the inner wire 6 and the suture slot 7 as shown in FIG. 9. In particular, a section of the suture 6 rests in a recess or suture capture zone 7d formed in the walls 7e, 7f of the needle 5.

Figure 10:
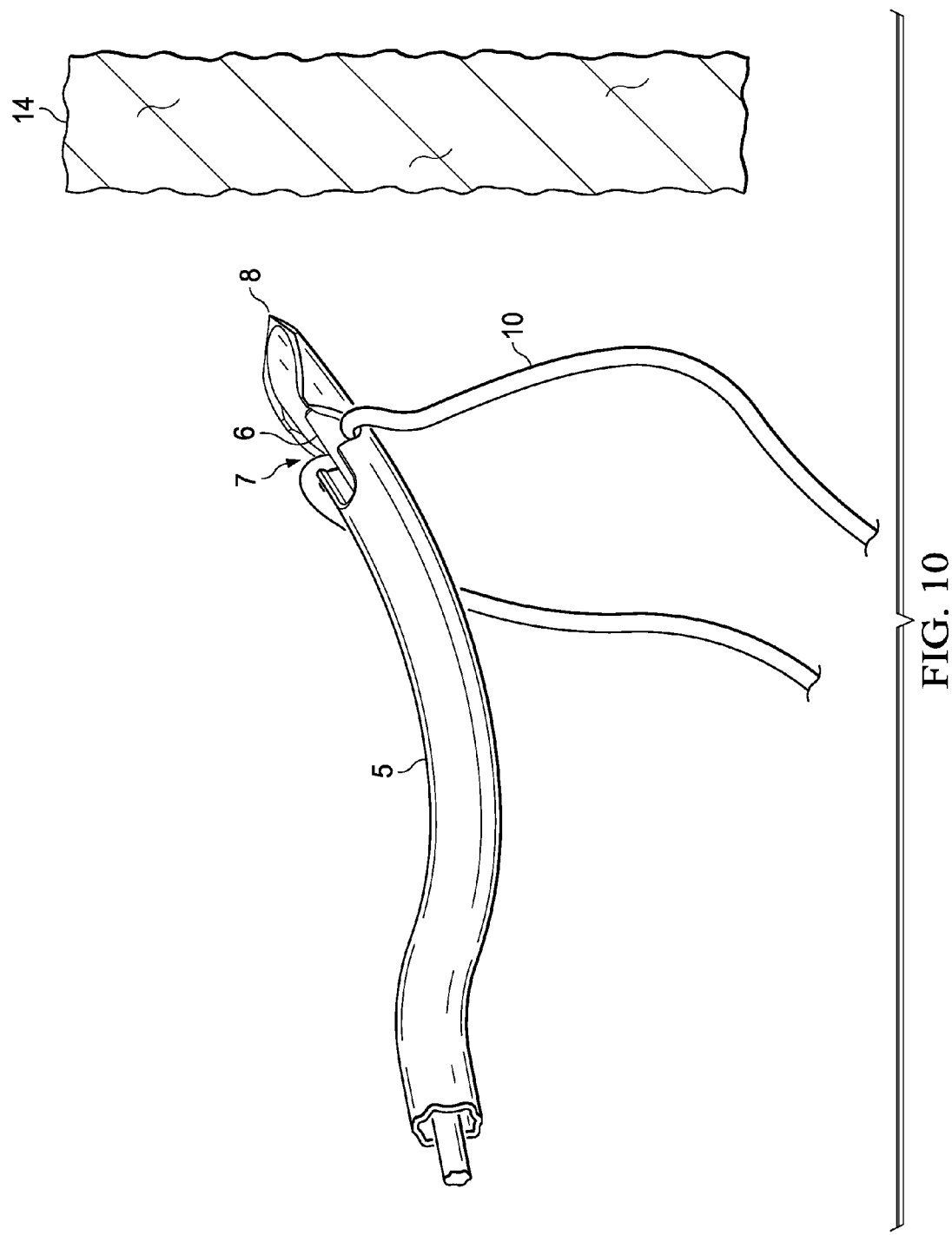

The inner wire 6 is then refracted thereby clamping, pinning or trapping the suture 10 between the inner wire 6 and the needle 5 as shown in FIG. 10.

Figure 11:
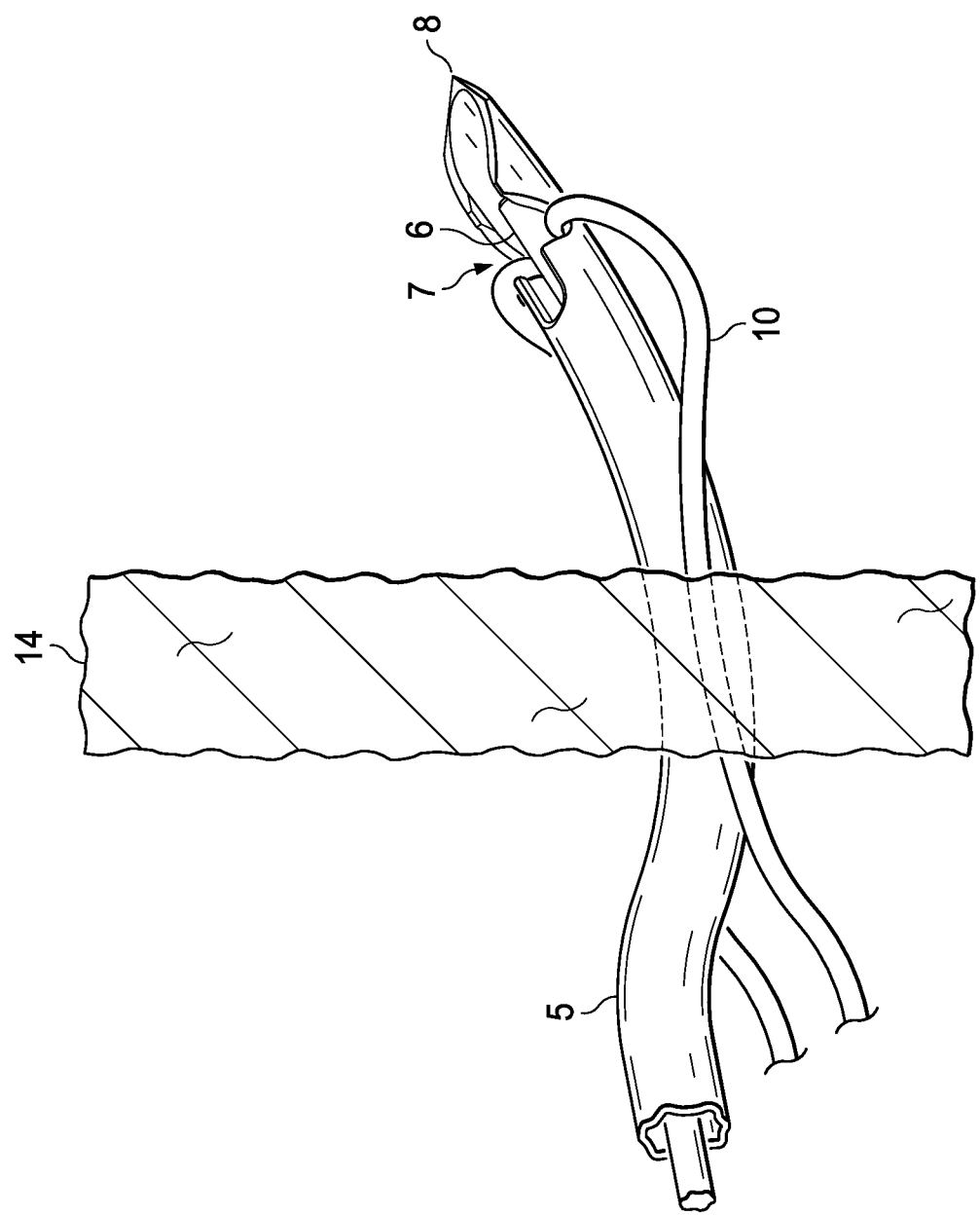

FIG. 11 shows piercing the tissue using the needle tip 8, thereby carrying the suture through the tissue.

Figure 12:
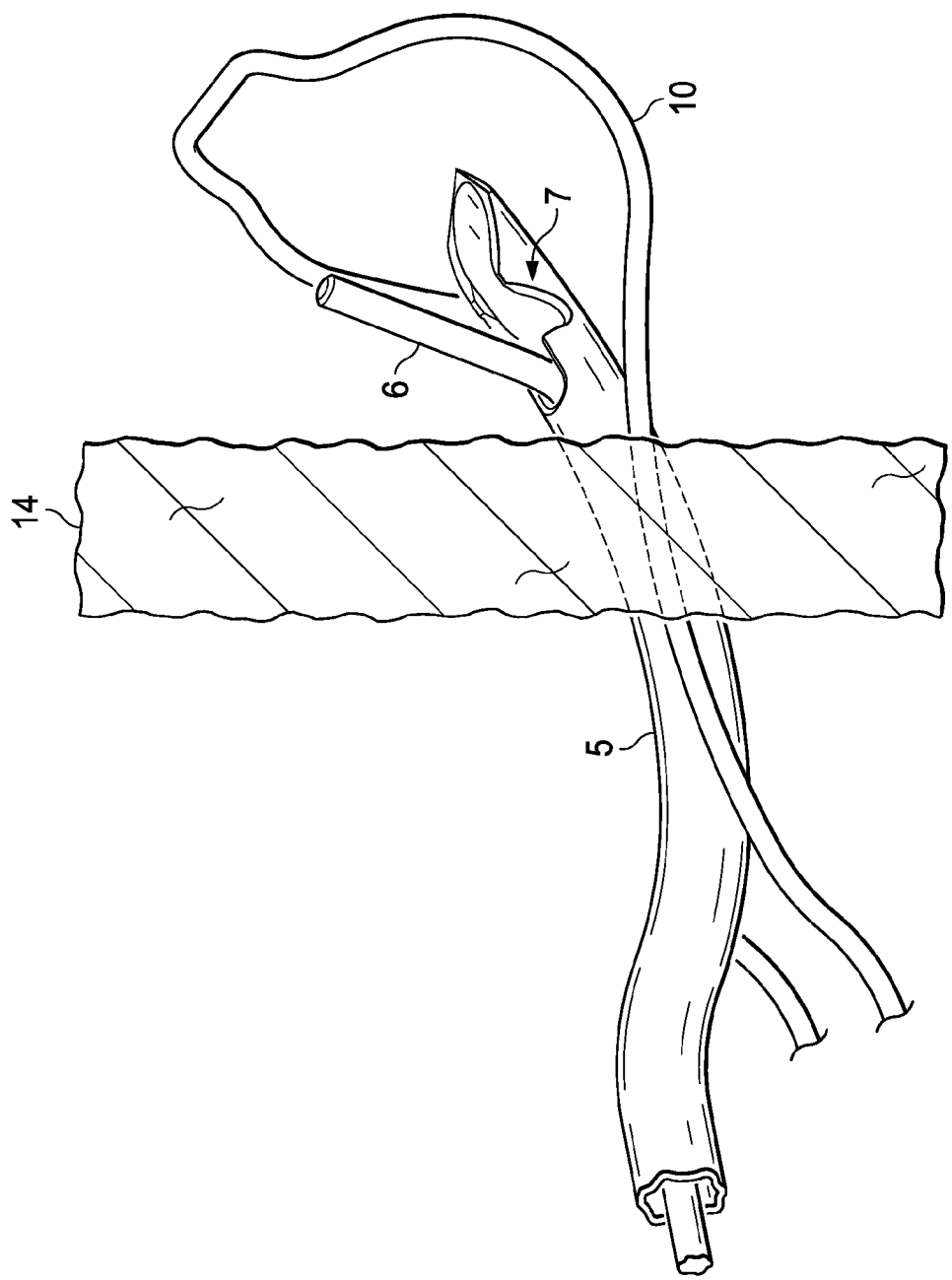
Figure 13:
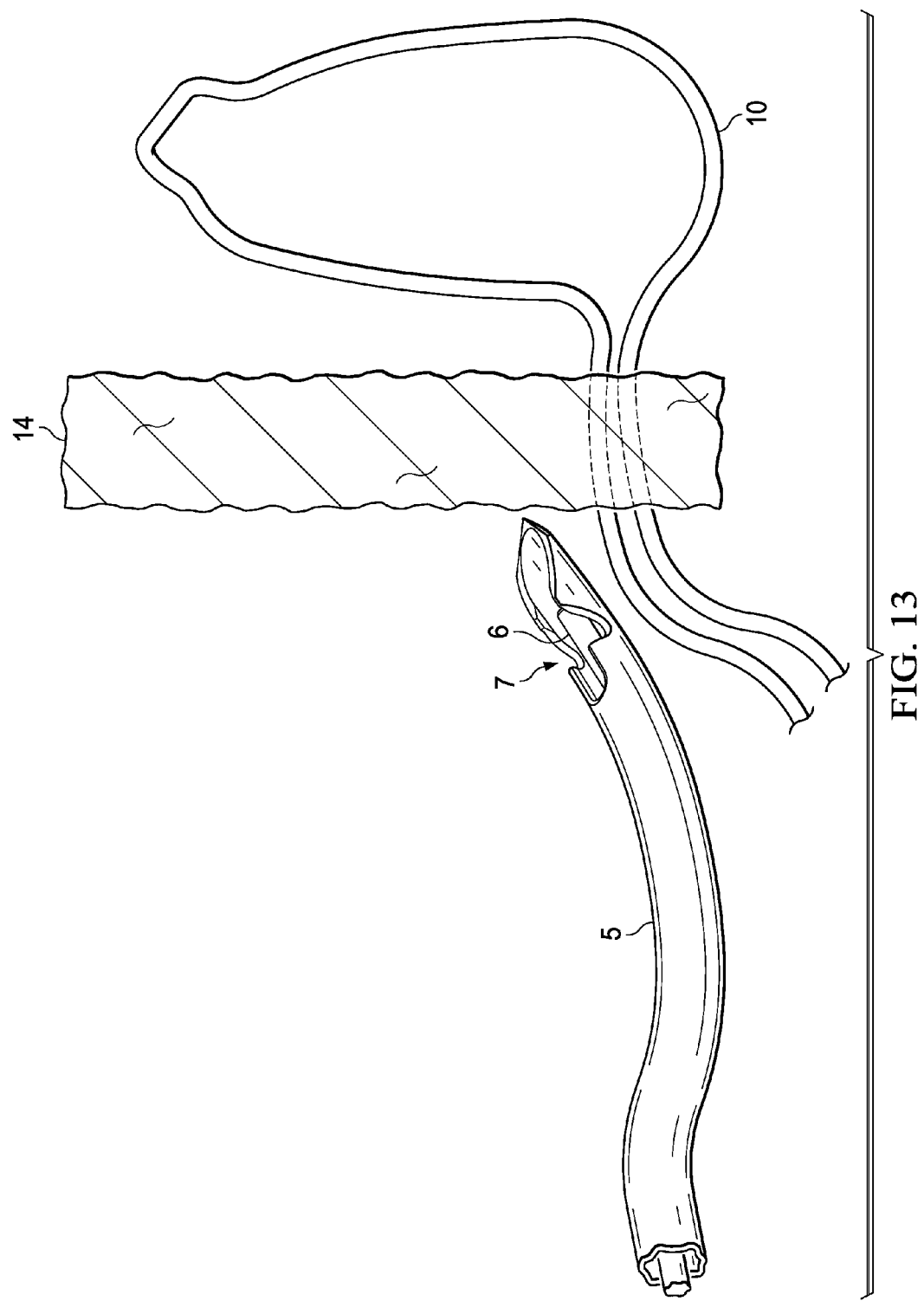
Figure 14:
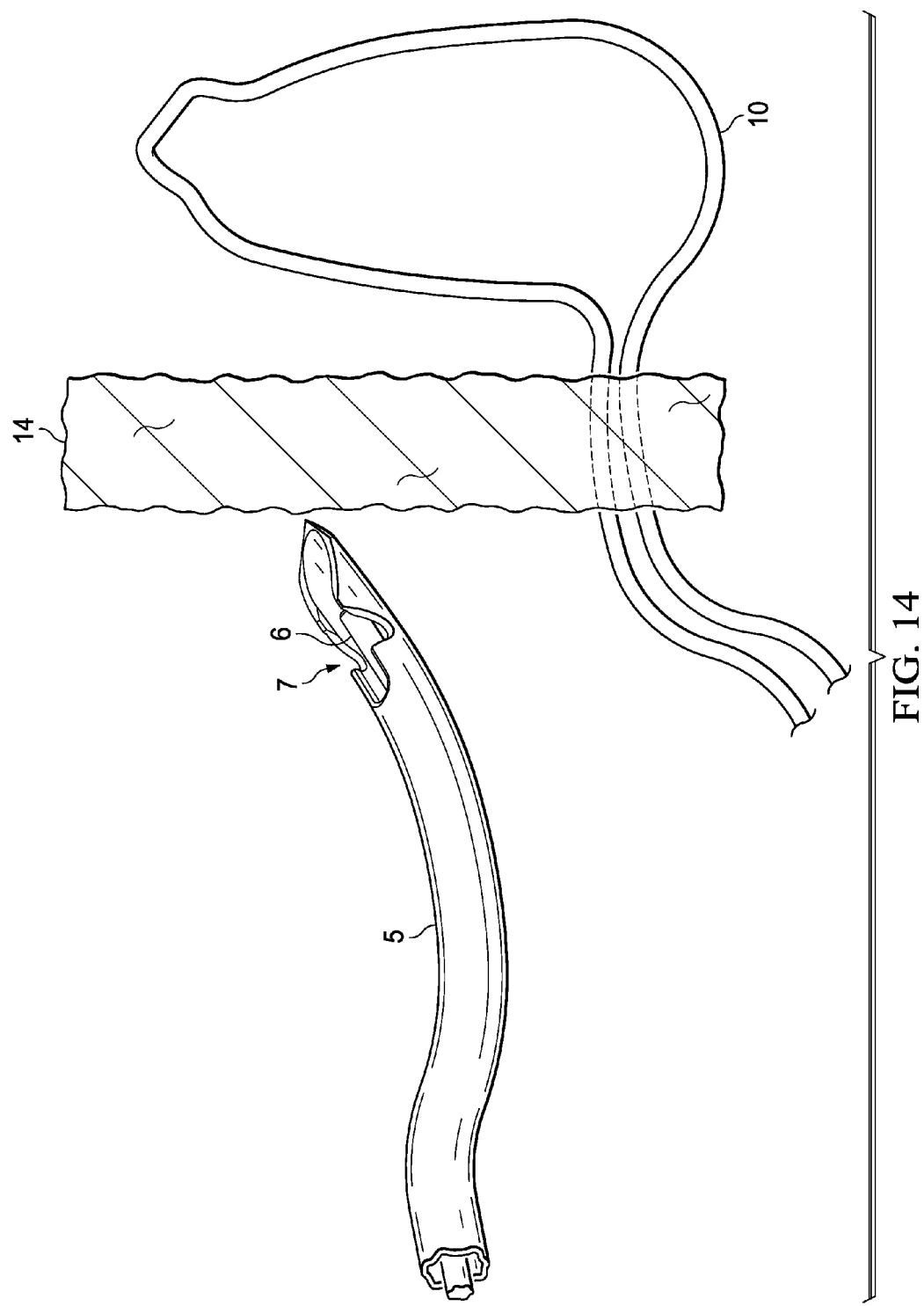

The inner wire 6 is then deployed to release the suture 10, retracted, and then the instrument is pulled back out of the tissue 14 as shown in FIGS. 12 and 13. Consequently, a section of suture is left extending through the tissue.

FIGS. 14 to 18 show one possible method of using the current embodiment to retrieve the suture that had previously been passed in order to form a stitch. Once the suture 10 has been passed through the tissue 14 the instrument is used to pierce the tissue 14 at a second location, different from the first location.

Figure 15:
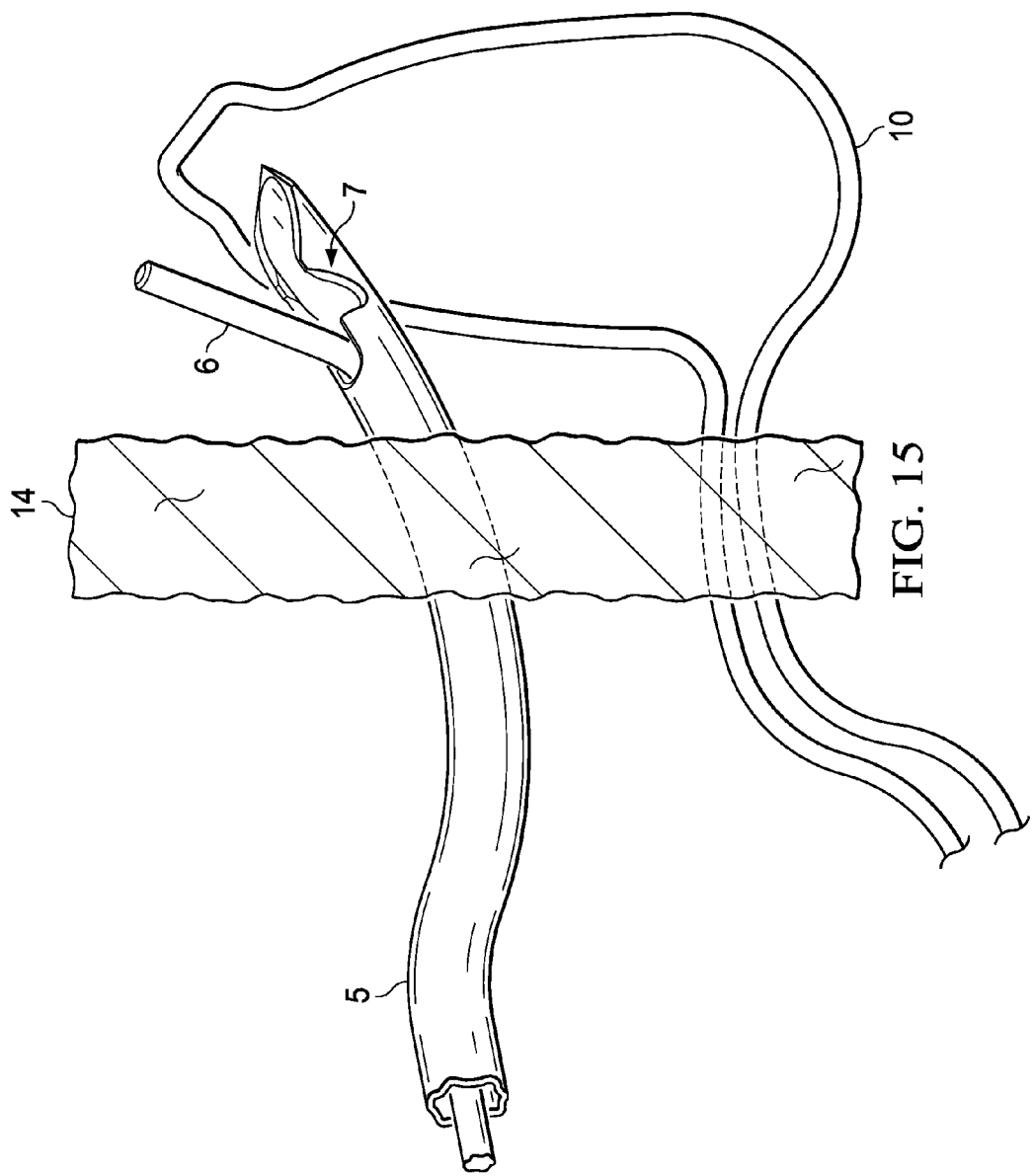

FIG. 15 shows the inner wire 6 deployed in order to create spacing between the inner wire 6 and suture slot 7.

Figure 16:
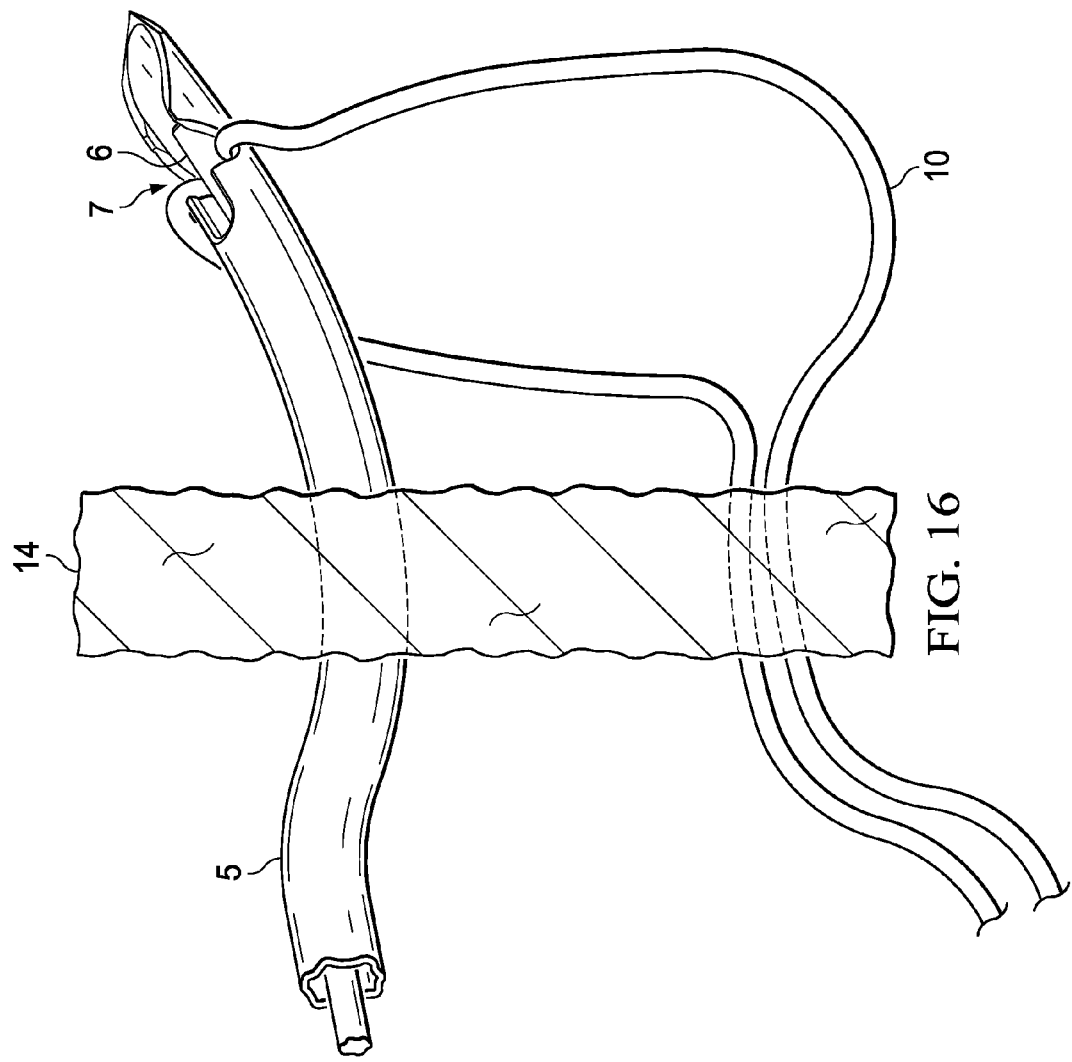

With reference to FIG. 16, the device is manipulated in order to position the suture 10 between the inner wire 6 and the needle 5. The inner member 6 is then retracted to secure the suture 10.

Figure 17:
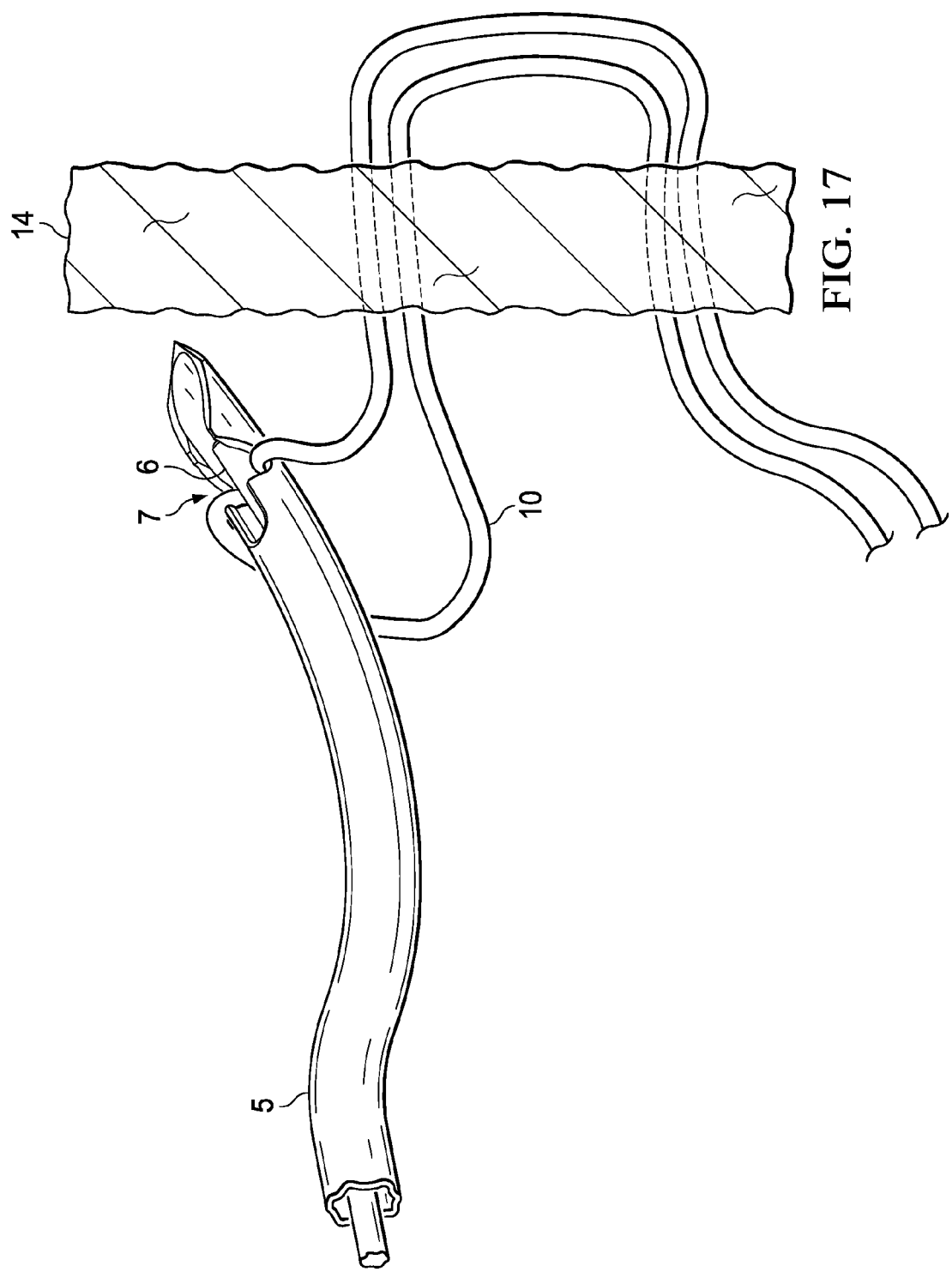

FIG. 17 shows the distal working section of the needle 5 pulled back out of the tissue 14 creating a stitch in the tissue.

Figure 18:
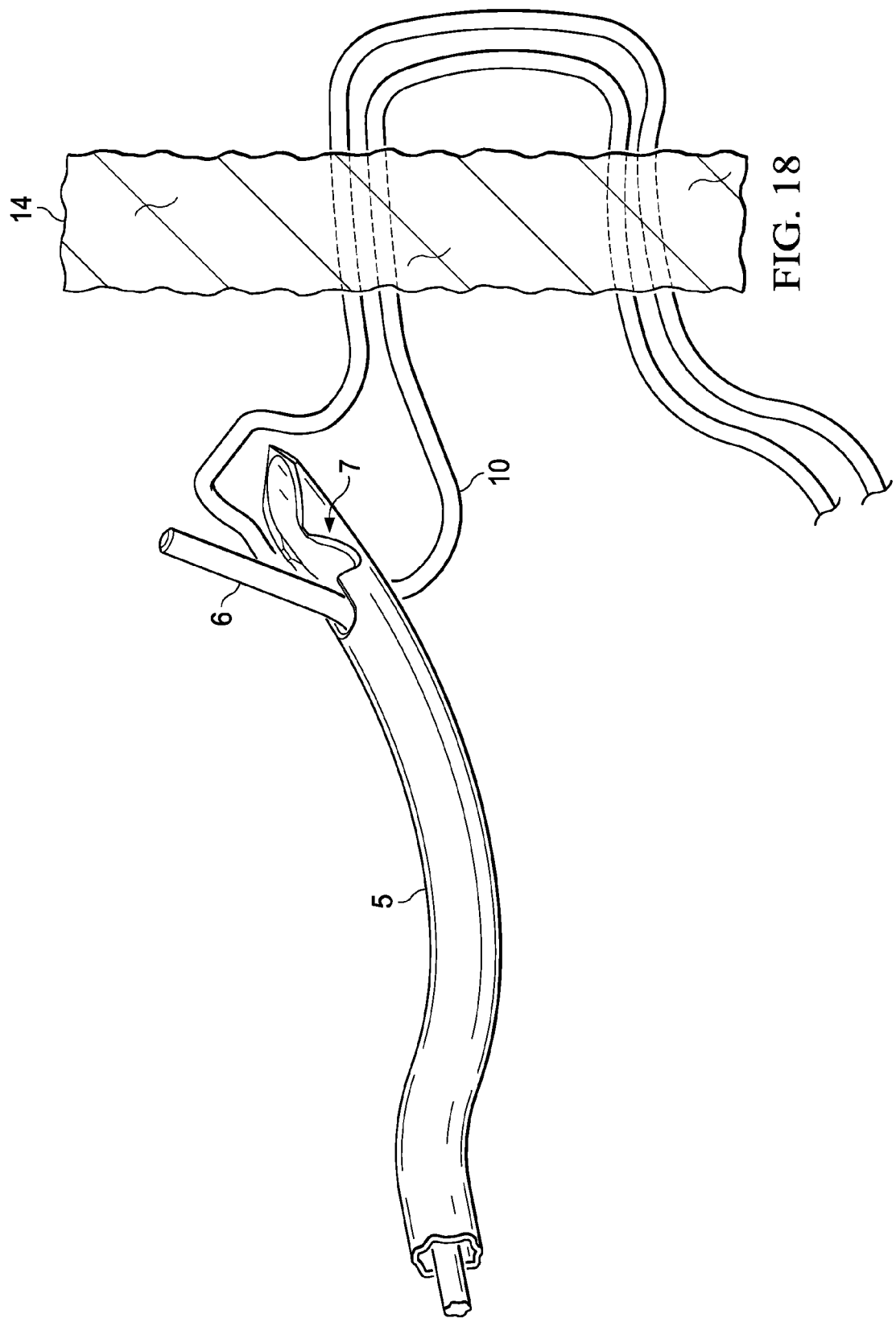

FIG. 18 shows the inner member in an extended position thereby releasing the suture 10 from the instrument.

Alternative Configurations

The working end 4 of the needle 5 can be formed into a variety of profiles including, but not limited to those illustrated in FIGS. 19 to 21.

Figure 19A:
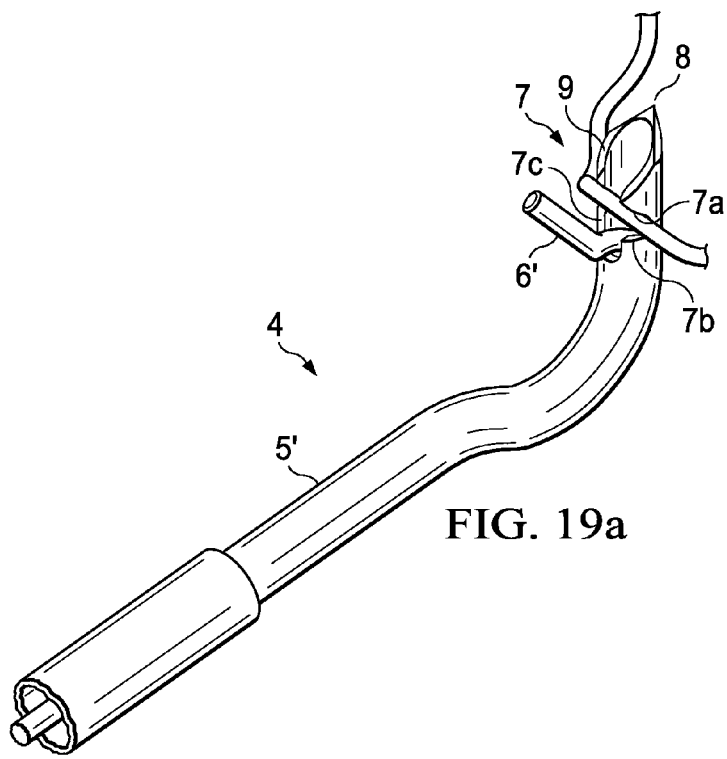
FIGS. 19a-19b are perspective views of the working end of another suture manipulating instrument in an extended configuration and a suture grasping configuration respectively.
Figure 19B:
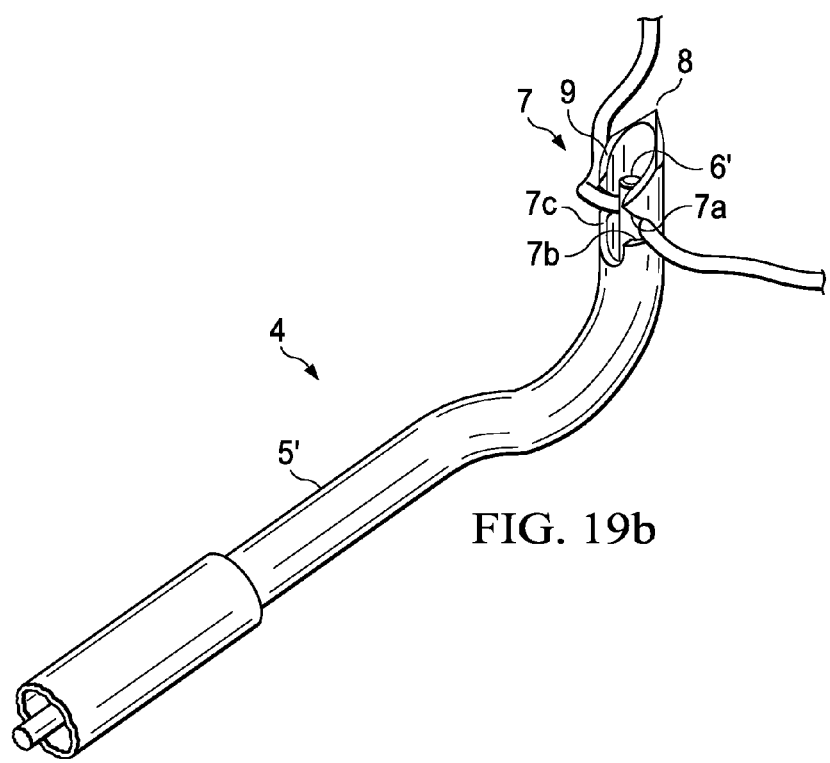

FIGS. 19a-19b show needle 5' having a relatively sharp upwards facing turn. This "Up" version is shown at about 90°. FIG. 19a shows inner wire 6' in a deployed or extended state. And FIG. 19b shows inner member 6' in a retracted suture clamping state.

Figure 20A:
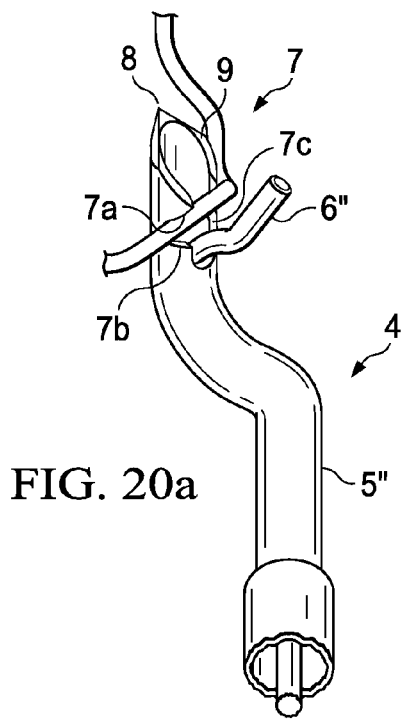
FIGS. 20a-20b are perspective views of the working end of another suture manipulating instrument in an extended configuration and a suture grasping configuration respectively.
Figure 20B:
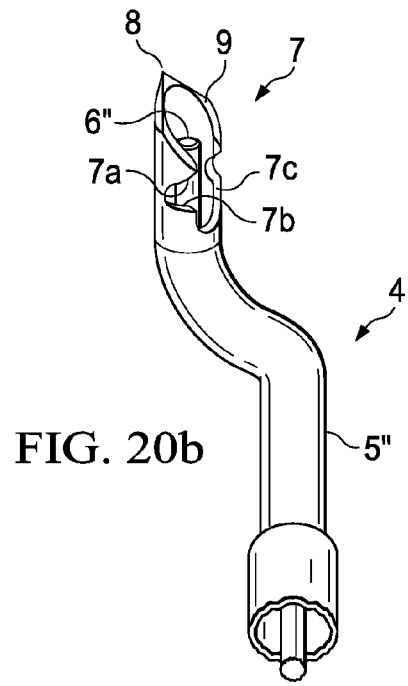

It is to be understood that the shape of the needle may vary. FIGS. 20a-20b, for example, show another needle shape. In particular, the embodiment shown in FIGS. 20a-20b is a 45° "Left" version. Inner member 6" is shown extended in FIG. 20a, and retracted in FIG. 20b.

Figure 21A:
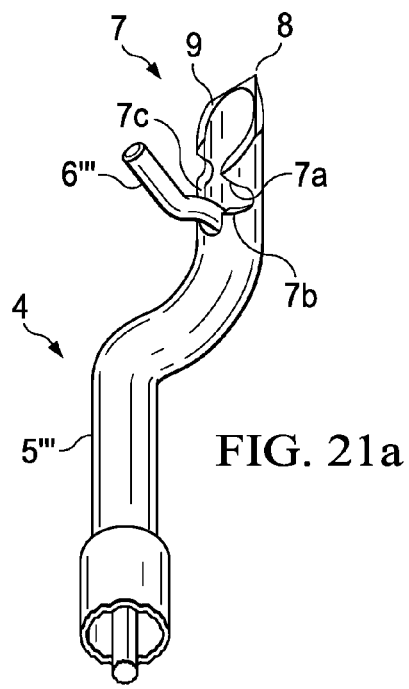
FIGS. 21a-21b are perspective views of the working end of another suture manipulating instrument in an extended configuration and a suture grasping configuration respectively.
Figure 21B:
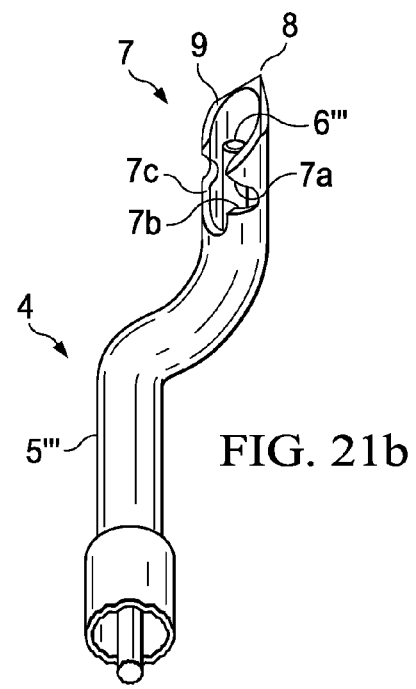

FIGS. 21a-21b show a 45° "Right" version. The inner member is shown extended in FIG. 21a, and retracted in FIG. 21b.

The suture slot 7 can be configured into a variety of profiles including, but not limited to those illustrated in FIGS. 22a to 22d.

Figure 22A:
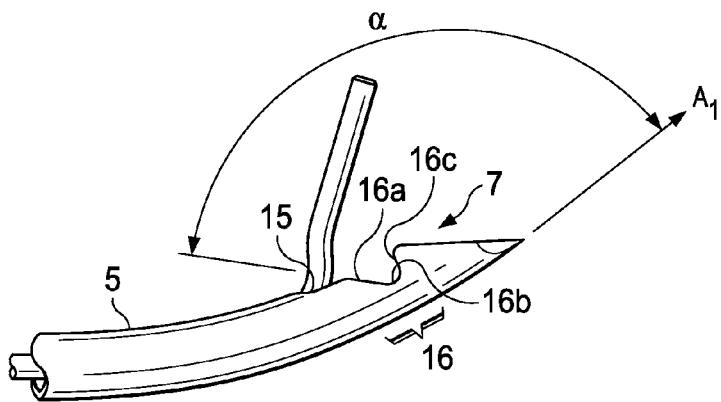
FIGS. 22a-22d are partial side views of suture manipulating instruments having various needle slot configurations.

FIG. 22a shows a suture slot 7 in the body of a needle 5. The slot 7 comprises a plurality of sections or regions. In particular, the suture slot 7 shown in FIG. 22a includes a wire relief area 15 (also shown, for example, in FIG. 34a and indicated by reference numeral 15') and a suture holding area 16. Suture holding area 16 comprises a proximal ramp 16a, a base 16b, and a distal surface 16c. Proximal ramp 16a is shown having an angle ($\alpha$) with needle axis (A1). Angle ($\alpha$) is shown having an angle of about 135 degrees, however, the angle ($\alpha$) may vary. Preferably, angle ($\alpha$) is equal to or greater than 90 degrees, and more preferably ranges from 90-135 degrees. Proximal ramp may be vertical.

Figure 22B:
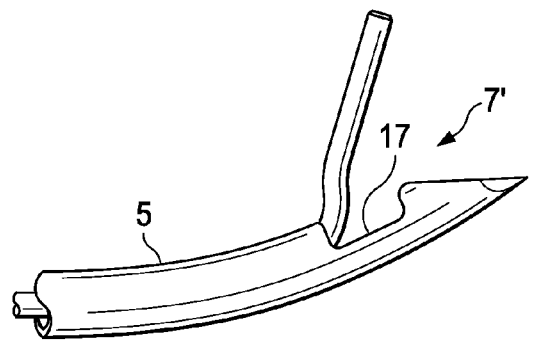

FIG. 22b shows another suture slot 7' with a rectangular profile and flat bottom or base 17.

Figure 22C:
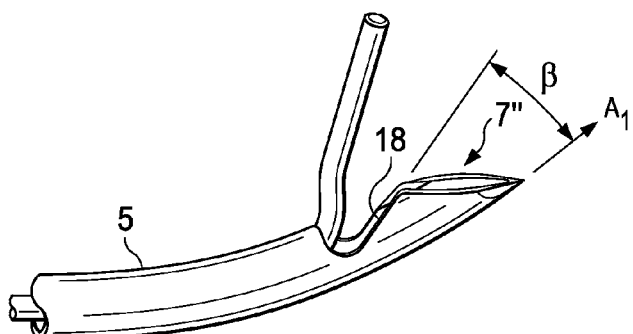

FIG. 22c shows a suture slot 7" with a distal ramp 18 and without a proximal slot or wire relief region. Distal ramp 18 is shown having an angle ($\beta$) with needle axis (A1). Angle ($\beta$) is shown having an angle of about 30 degrees, however, the angle ($\beta$) may vary. Preferably, angle ($\beta$) is less than 90 degrees, and more preferably from 20-65 degrees.

Additionally, though not shown in FIGS. 22a-22c, slot 7 may include both distal and proximal ramps.

Figure 22D:
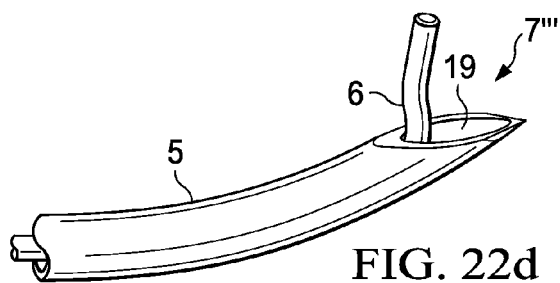

Additionally, although a preferred embodiment of the present invention includes a laterally disposed slot comprising a recess, the presence of such a slot is not essential. FIG. 22d, for example, shows an a needle 5 comprising an inner member 6 extending from an opening 19. A suture (not shown) may be clamped or pinned between the inner wire member 6 and the bevel opening 19. Bevel opening 19 does not include a suture holding region or recess in its side walls as shown in other embodiments described herein.

Figure 23A:
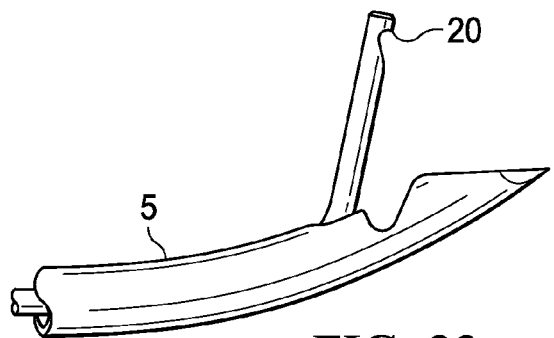
FIGS. 23a-23c are partial side views of suture manipulating instruments having various wire configurations.
Figure 23B:
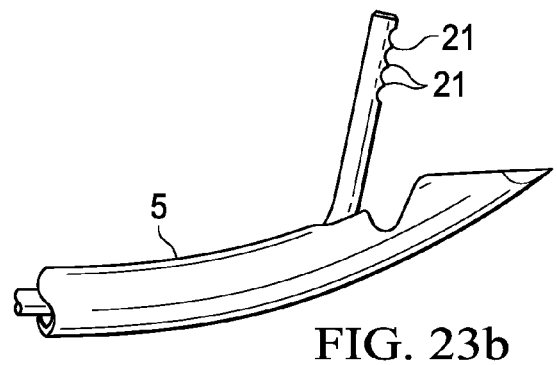
Figure 23C:
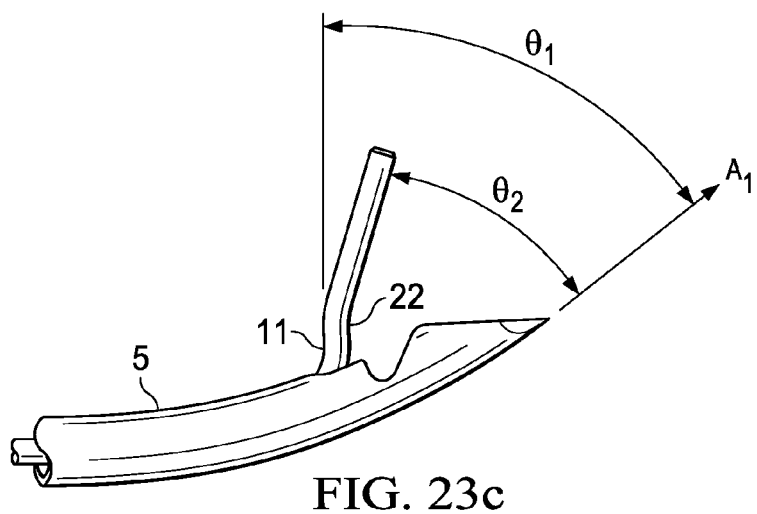

The distal end of the inner member can be configured into a variety of profiles including, but not limited to those illustrated in FIGS. 23a-23c. FIG. 23a shows the inner member as a single wire having a single tooth 20 proximal to the tip of the inner wire. FIG. 23b shows the inner wire with multiple teeth 21 proximal to the tip of the wire. The teeth pattern can be added to improve hold strength on the suture. Other options to improve grip on the suture include, but are not limited to surface treatments of the wire that may add or remove material to roughen the surface of the wire. The height of the teeth may range from 0.1-0.5 mm depending on the size of the inner member.

FIG. 23c shows another possible configuration for the working end of the inner wire in which the wire has two or more bends at the working end. In this instance the wire is configured with a first bend 11 and a second bend 22. First bend is shown being proximal to second bend 22. Preferably, but not necessarily, the first bend is proximal to the tip of the inner wire 6 by a first distance ranging from 2-7 mm. Preferably, but not necessarily, the second bend is proximal to the tip of the inner wire 6 by a second distance ranging from 0.5-3 mm.

First and second bends are shown forming angles $\theta_1$ and $\theta_2$ with the needle axis A1, respectively. $\theta_2$ is less than $\theta_1$. $\theta_1$ preferably ranges from 30-90 degrees. $\theta_2$ preferably ranges from 0-45 degrees.

Figure 24A:
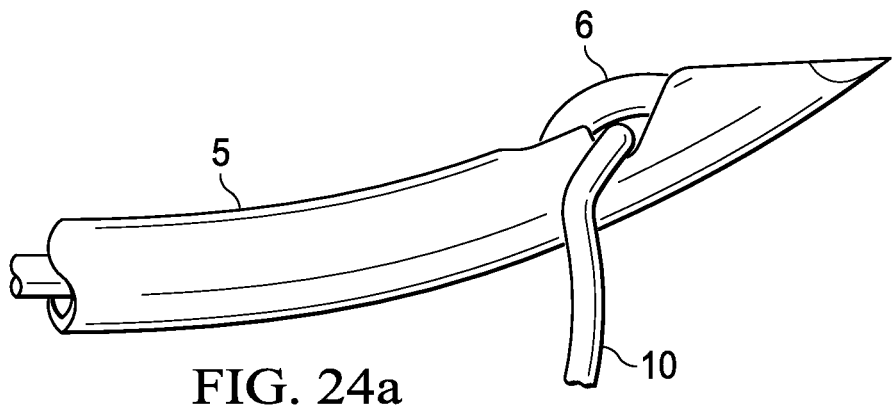
FIGS. 24a-24b are side and cross sectional views respectively of the working end of a suture manipulating instrument in a retracted configuration.
Figure 24B:
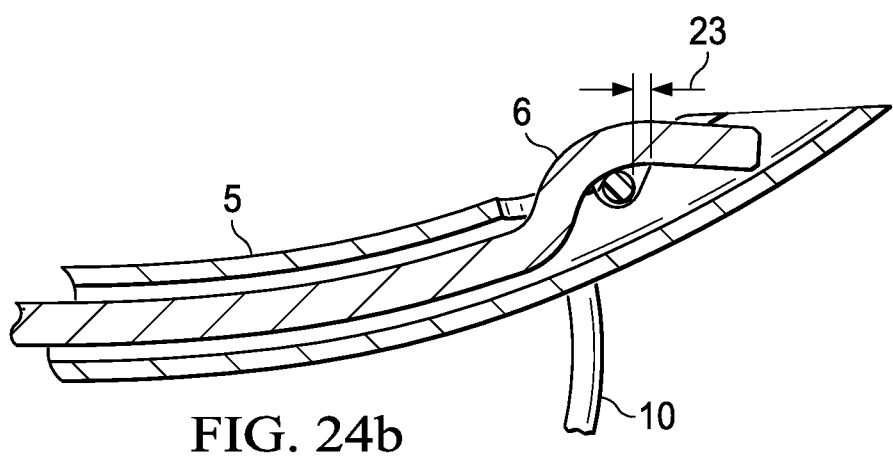

This configuration of the instrument can be used to produce a gap, space or clearance 23 between the inner wire, suture, and needle to allow the suture to slide while still being trapped in the working end for suture manipulation as shown in FIGS. 24a-24b.

In embodiments, the inner member is sufficiently flexible such that further retraction of the inner member further clamps the suture within the slot such that the suture may not slide. The instrument in such embodiments comprises an extended configuration, a suture lock or clamping configuration, and an intermediate suture sliding configuration as shown in FIGS. 24a-24b.

Figure 27C:
FIGS. 27c-27d are side and cross sectional views respectively of the working end of the suture manipulating instrument shown in FIGS. 27a-27b in a suture grasping configuration.
Figure 27D:
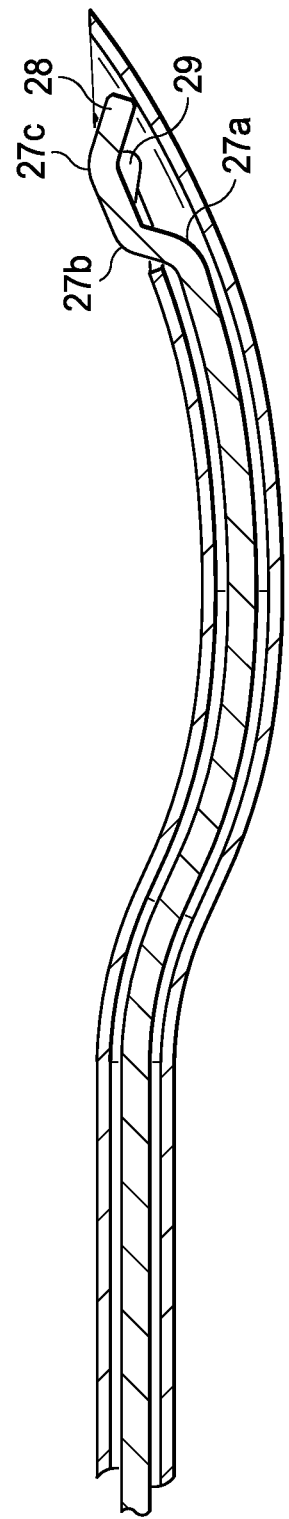
Figure 28A:
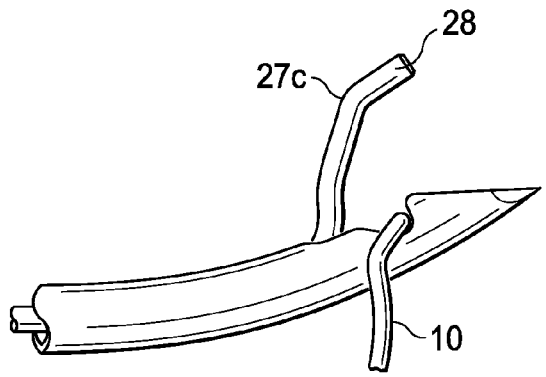
FIGS. 28a-28b are side views of the working end of another suture manipulating instrument in an extended configuration and a suture grasping configuration respectively.
Figure 28B:
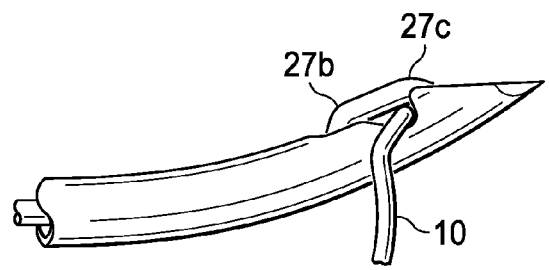
Figure 28C:
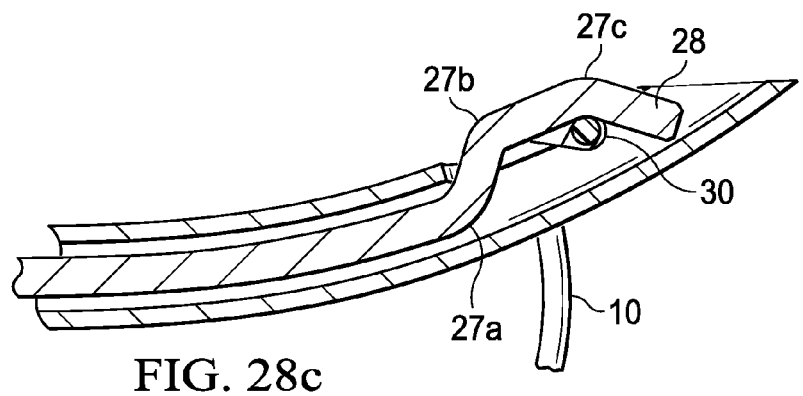
FIG. 28c is an enlarged cross sectional view of the suture instrument holding the suture shown in FIG. 28b.

With reference to FIGS. 27 to 28, a working distal section of an inner member is shown including three bends, 27a, 27b, and 27c. The $3^{rd}$ bend 27c being positioned near or at the distal tip. Wire member also includes a straight portion 28.

The implementation of multiple bends may be used to facilitate suture sliding. For example, while in the retracted state shown in FIGS. 27d and 28c, the working end of the inner wire and the needle slot could constrain the suture 10 while providing a clearance 29 and 30, respectively, necessary to allow the suture 10 to slide.

Further retracting the inner wire would force the wire to close further thereby pinning the suture. Consequently, in accordance with certain embodiments of the invention, a suture instrument is operable in a plurality of configurations including 1) a deployed or extended configuration in which the inner member extends from the needle creating a space between the inner member and needle, 2) an intermediate or suture sliding position in which the inner member is retracted to a degree such that the suture is slidably held across the needle slot, and 3) a pinned or suture clamped configuration in which the inner member is more fully retracted such that the suture is compressed into the slot and in a tortuous manner to firmly grasp the suture and prevent the suture from sliding. Amongst other things, adding multiple bends to the inner member serves to facilitate in deployment or retraction when implemented with various needle shapes.

Manufacture

The needle can be constructed from a variety of materials or combinations of materials, including but not limited to metals such as stainless steel and titanium, plastics such as polycarbonate and PEEK, or shape memory or super elastic Nitinol.

Similarly, the inner wire can be constructed from a variety of materials or combinations of materials, including but not limited to metals such as stainless steel and titanium or plastics such as polycarbonate and PEEK. The preferred embodiment is shape memory or superelastic Nitinol.

The working end of the needle and inner member preferable has circular cross-sections, though other cross-sectional shapes might also be employed. Other shapes include but are not limited to square, rectangular and ovalized cross-sections.

Figure 25:
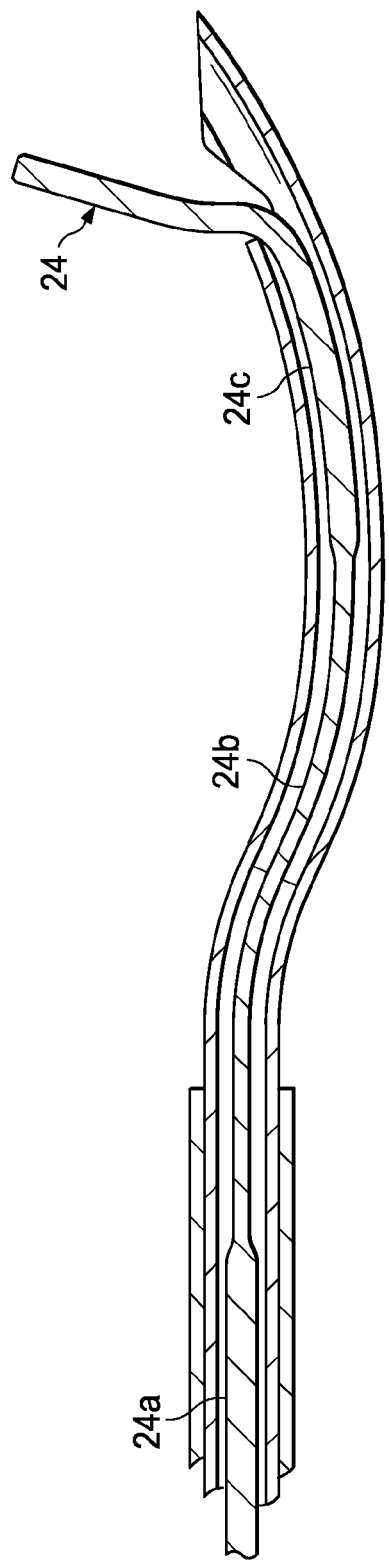
FIG. 25 is a cross sectional view of the working end of another suture manipulating instrument in an extended configuration.

The cross-sectional area of the inner member may be constant or vary along its length. For example, the inner member can be round at the proximal end and flat at the distal end. The inner member may start off at one diameter and taper down to a lower diameter. FIG. 25, for example, shows an embodiment of the invention comprising an inner member 24 having a proximal section or first diameter section 24a, a second or reduced diameter section 24b, and a third most distal section having an enlarged diameter 24c. In embodiments, the diameter of the inner member ranges from 0.75-2 mm. In embodiments, the ratio of the diameter of section 24a to section 24b ranges from 25-75%.

Figure 26:
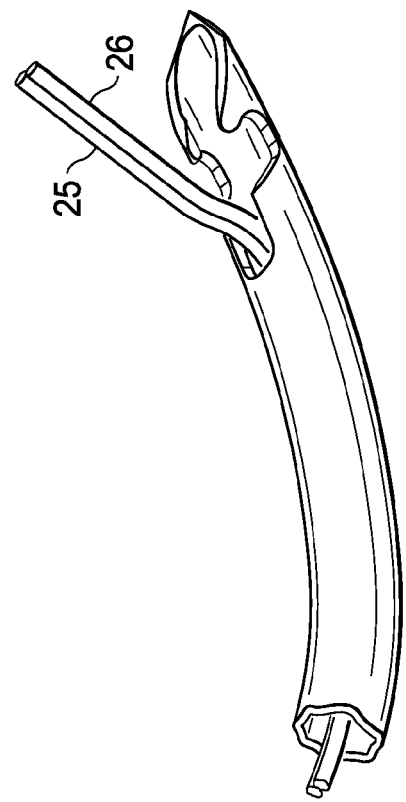
FIG. 26 is a perspective view of the working end of another suture manipulating instrument in an extended configuration.

The inner member can be a single wire or filament. Additionally, the inner member may comprise a wire bundle including two or more wires as shown in FIG. 26. For example, two wires 25 and 26 may be used to perform the same function as a single larger wire member. Implementing multiple wires would allow the wires to translate more easily through the needle while maintaining the rigidity necessary to retain suture. The wires can be attached or detached at the ends or along the length of the wire by adhesives, bonds, fusing, and other attachment techniques known to those of skill in the art.

Figure 29A:
FIGS. 29a-29b are side and perspective views respectively of the working end of another needle distal section and inner member in an extended configuration.
Figure 29B:
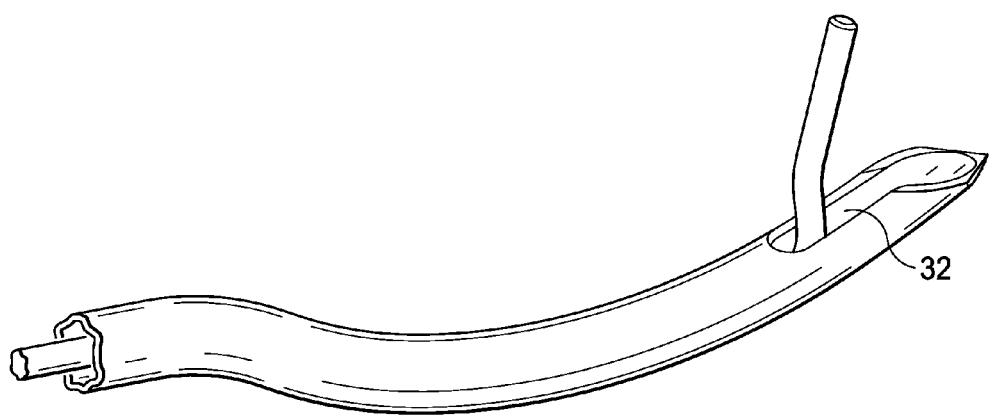

As described herein the working end of the needle may have a wide variety of shapes and configurations. FIGS. 29a-b show a needle body distal section 31 comprising a single slit 32 which would allow the inner wire to deploy from the needle. Single slit 32 preferably, but not necessarily, is wide enough to allow suture to engage with the inner wire and needle in a similar manner to that illustrated in FIGS. 6 and 7. Single slit 32 differs from some of the needle configurations described herein in that a suture holding region or recess in the needle walls is absent in the single slit (e.g., single slit lacks the suture holding region 16 of FIG. 22a).

Figure 30A:
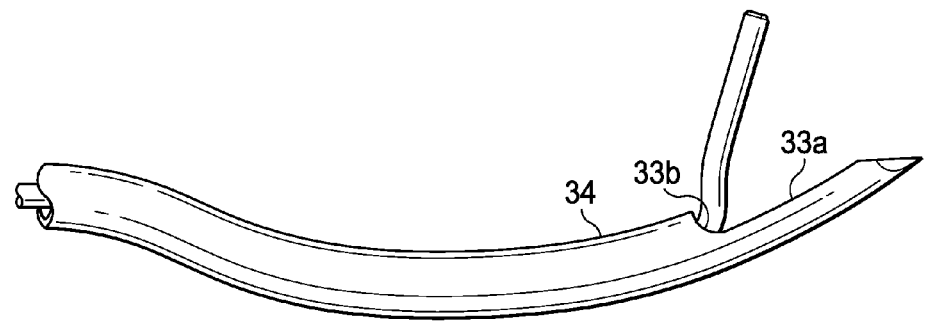
FIGS. 30a-b are side and perspective views respectively of the working end of another needle distal section and inner member in an extended configuration.
Figure 30B:
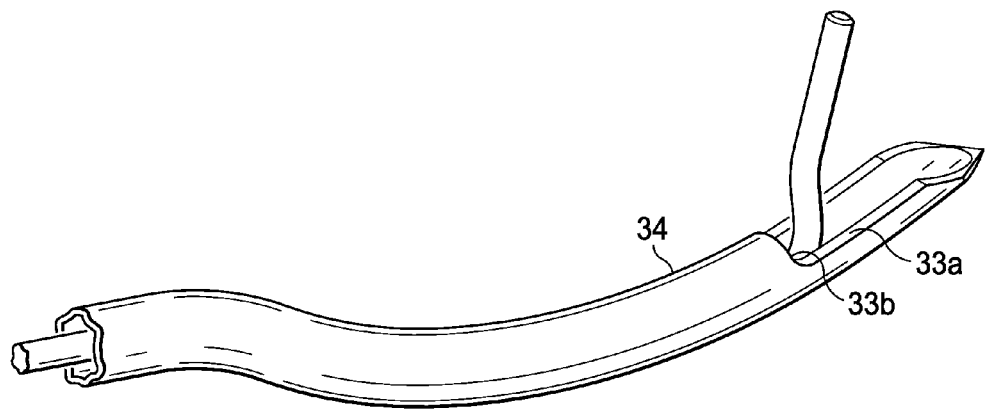
Figure 30C:
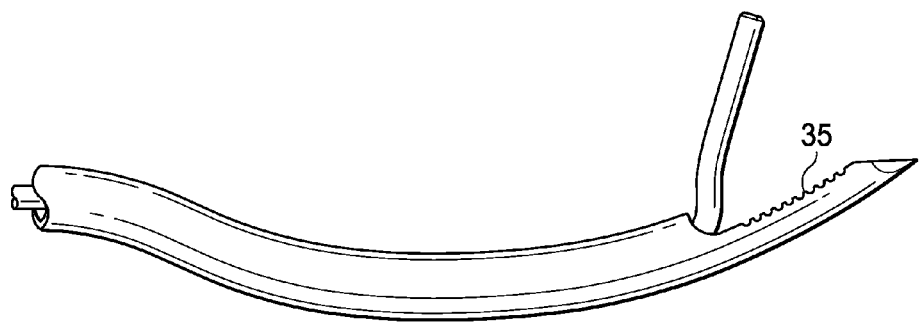
FIG. 30c is a side view of the working end of another needle distal section and inner member in an extended configuration.

FIGS. 30a-30b show a working end of the needle body 34 comprising a single cutoff 33a with a shoulder 33b. This configuration would allow relief for the inner wire while still providing a constraining path for the suture (see, e.g., FIGS. 6 to 7). Additionally, as shown in FIG. 30c, the cutoff may have serrations 35, a roughened surface via for example a surface treatment, or another grip feature in order to provide added suture retention force.

Figure 31A:
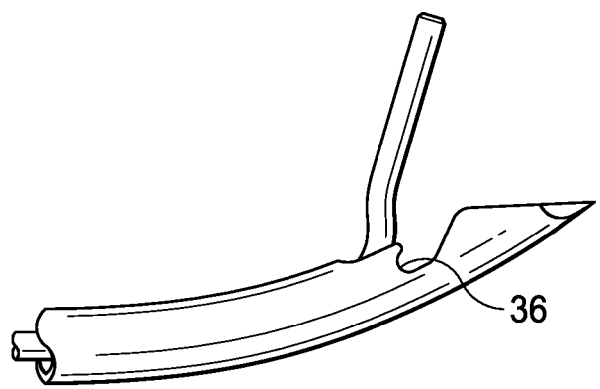
FIG. 31a is a side view of the working end of another needle distal section and inner member in an extended configuration having a proximal undercut.
Figure 31B:
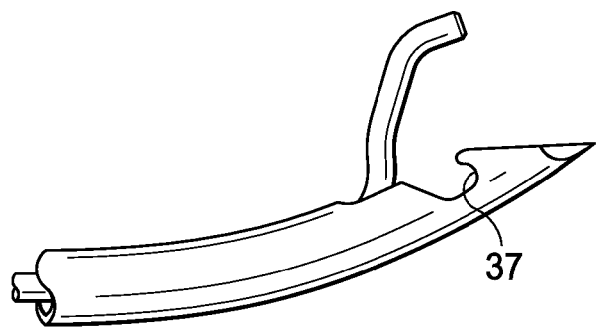
FIG. 31b is a side view of the working end of another needle distal section and inner member in an extended configuration having a distal undercut.
Figure 31C:
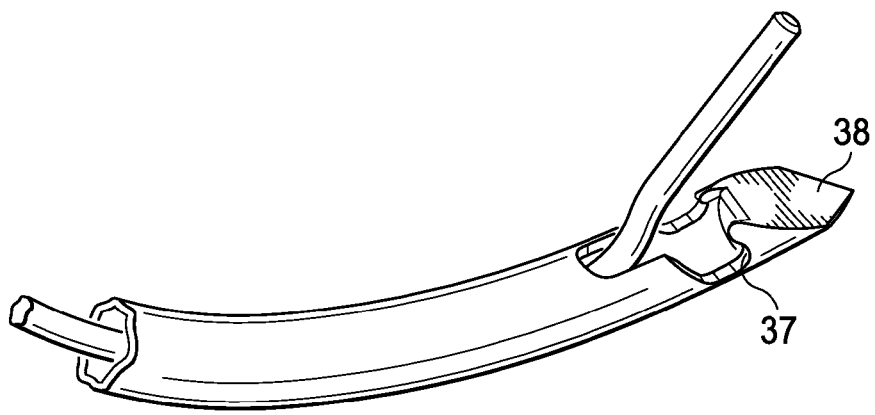
FIG. 31c is a perspective view of the working end of another needle distal section and inner member in an extended configuration having a distal undercut.

FIGS. 31a-31c illustrate additional possible configurations for the suture slot at the working end of the needle in which a hook or undercut may be used to facilitate suture retention and or manipulation. FIG. 31a shows a suture slot with a proximal hook/undercut 36. The undercut 36 is formed in the wall of the needle body Inner member is shown having two bends in this embodiment.

FIG. 31b shows a suture slot comprising a distal hook/undercut 37. Inner member is shown having three bends in this embodiment.

In embodiments, the needle may comprise a hollow or solid tip or end. FIG. 31c shows a suture slot with a distal hook/undercut 37 and a solid needle tip 38. The solid tip may facilitate tissue penetration. The solid tip may also work in conjunction with the inner wire to form clearance for suture sliding with or without multiple bends at the working end of the inner wire. The solid tip can be formed by a variety of methods including but not limited to filling in the needle tip with a solder or epoxy. A plastic rod can be bonded or mechanically attached within the inner diameter of the needle to form the solid tip. A metal rod can also be welded, bonded or mechanically attached within the inner diameter of the needle to form the solid tip.

The inner member shown in FIG. 31c includes two bends. However, as described herein the inner member may have one or more bends depending on the desirability of suture clamping force, and whether an intermediate suture sliding position is desired.

Figure 32A:
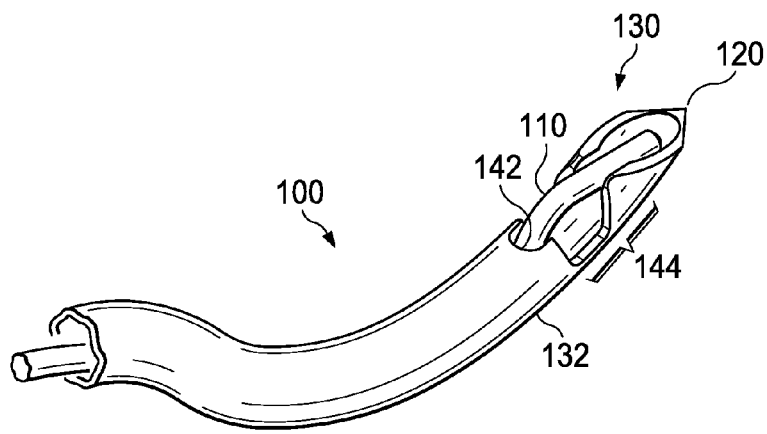
FIGS. 32a-32b are perspective and side views respectively of the working end of another needle distal section and inner member in a refracted configuration.
Figure 32B:
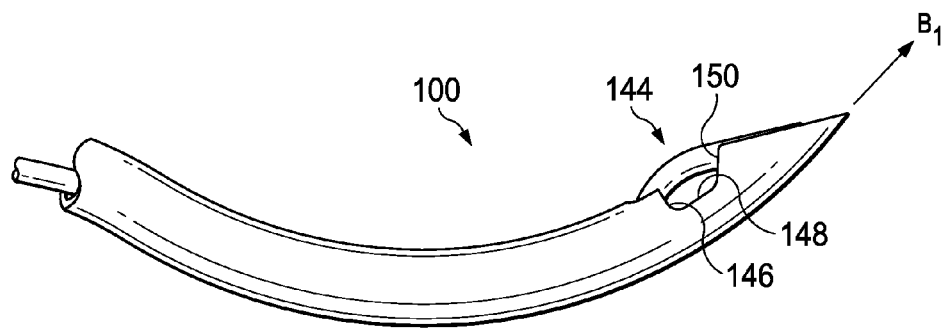
Figure 32C:
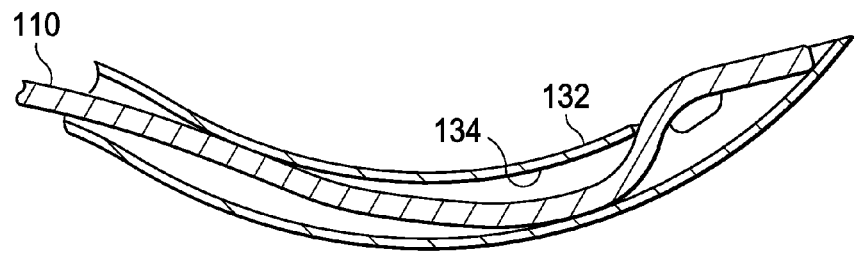
FIG. 32c is a cross sectional view of the needle distal section and inner member shown in FIG. 32b.

FIGS. 32a-32c illustrate another embodiment of a distal section of a needle 100 and inner member 110 in a retracted configuration. The distal section of the needle comprises a needle body 132 having a gently curved crescent shaped profile, a sharpened distal tip 120, and a lumen 134 extending therethrough.

As described herein the inner member 110 is operable to move from a retracted position to a deployed or extended position from the needle body. A suture not shown may be clamped or grasped between the inner member and needle when the inner member is in the retracted position.

The embodiment shown in FIGS. 32a-32c includes a suture slot 130. The suture slot 130 comprises a plurality of sections including a wire relief section 142, and a suture holding section 144. The inner member 110 is shown in a retracted position, and has an inner member tip portion disposed within slot 130.

With reference to FIG. 32b, suture holding section 144 is shown as a recess in the side walls or body of the needle 100. Suture holding section 144 comprises a proximal shoulder or surface 146, a base or trough section 148, and a distal ramp 150. The dimensions and angles and of the features are preferably in the range as described herein such as but not limited to the embodiments shown in FIG. 22.

As described herein, the suture holding region 144 serves to clamp the suture when the inner member is retracted. The degree of clamping may be bolstered by modifying the design including for example, material selection, increasing the width of the trough 148, increasing the number of bend angles present in the inner member, or increasing the degree of the bend angles of the inner member.

Additionally, suture release form the instrument may be facilitated by, amongst other things, decreasing the distal ramp angle so as to allow the suture to slide more freely out of the virtual jaw grip formed between the needle and the inner member. Many features of the described embodiments may be modified to achieve a desired design, result or application, and such modifications are intended to be part of the invention. The invention is intended only to be limited as set forth in the appended claims.

FIGS. 33-36 illustrate various constraining features to further hold the inner member, trapping the suture, when the suture instrument is in the retracted suture-clamping configuration.

Figure 33A:
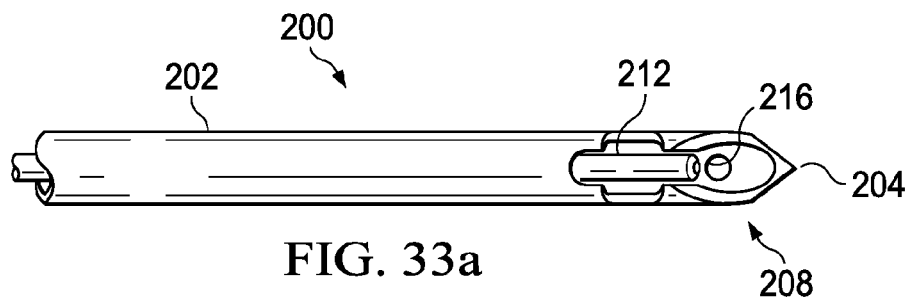
FIGS. 33a-b are top and cross sectional views respectively of the working end of another needle distal section and inner member in an extended configuration.
Figure 33B:
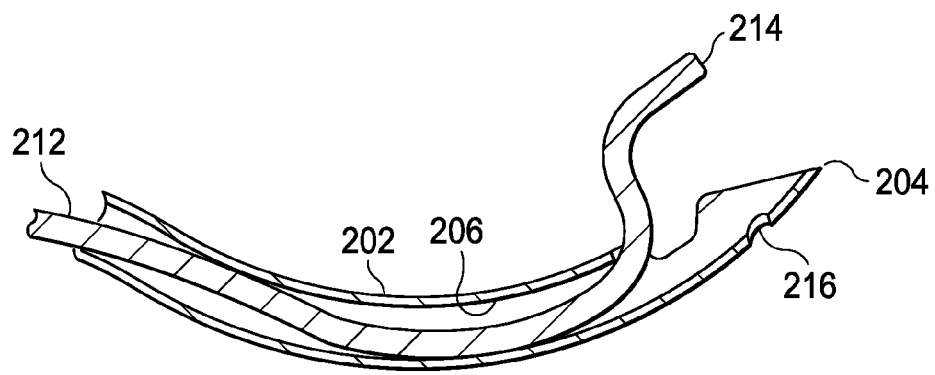

FIGS. 33a-33b illustrate a distal needle section 200 including a needle body 202, a tissue penetrating distal tip 204, a lumen 206 extending therethrough, and a suture slot 208. Inner member 212 is shown having a plurality of bends and in a deployed configuration. Inner member extends away from the needle body. As described herein, spacing the inner member away from the needle body as shown in FIGS. 33a-33b serves to create a space within which the suture (not shown) may be inserted or placed.

Figure 33C:
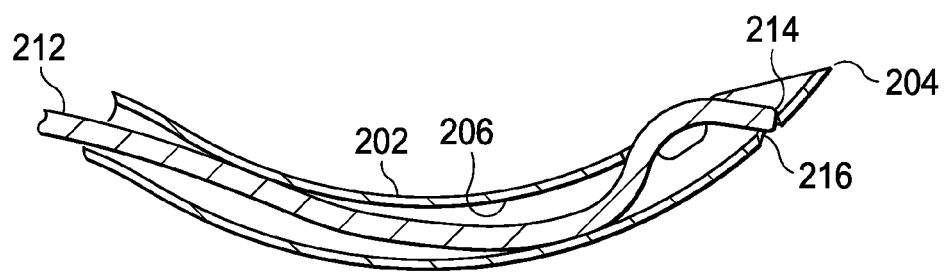
FIG. 33c is a cross sectional view of the needle distal section and inner member shown in FIG. 33b shown in a retracted configuration.

FIG. 33c shows inner member 212 in a retracted configuration. Distal section of the inner member is substantially disposed within the suture slot 208 and in particular, a distal tip or end 214 of the inner member is rotated or manipulated until it is fit within hole or aperture 216 in the needle body 202.

Figure 34A:
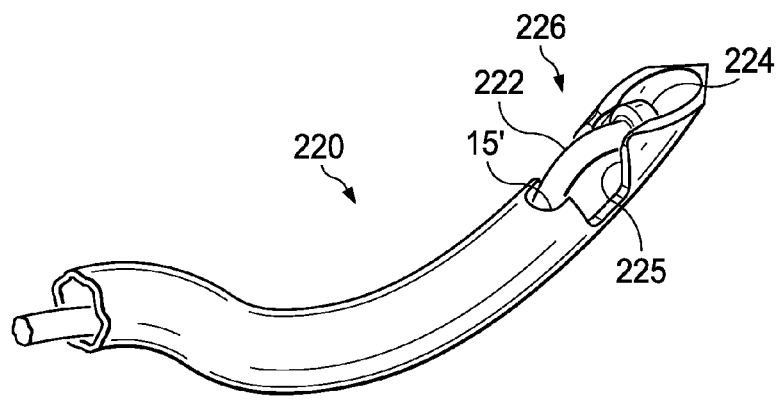
FIG. 34a is a perspective view of the working end of another needle distal section and inner member shown in a retracted configuration.
Figure 34B:
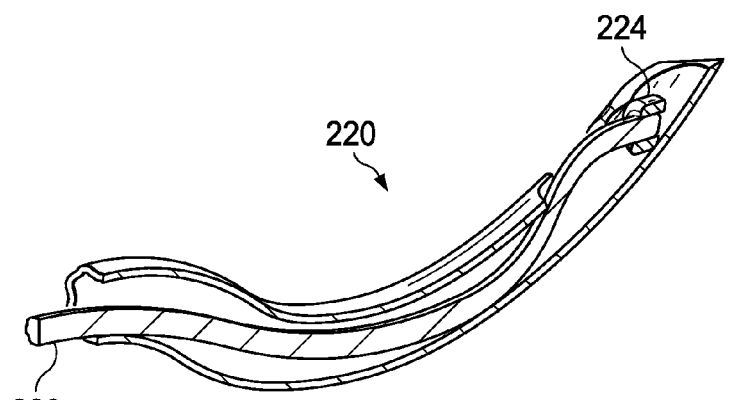
Figure 34C:
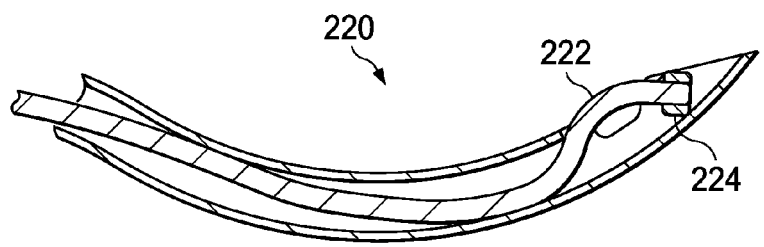

FIGS. 34a-34c show another needle distal section and inner member in a retracted configuration. The embodiment shown in FIGS. 34a-34c differs from that shown in FIGS. 33a-33c in that the embodiment shown in FIGS. 34a-34c includes a ferrel type constraining feature. In particular, ferrel 224 comprises a cylindrical body having a cavity to receive the tip of the inner member 222. Ferrel 224 may be bonded or otherwise affixed within the slot 226 of the needle section. The ferrule 224 is attached to the wire 222 and is pulled into the tube such that the ferrule restricts the wire from being pulled perpendicular to the needle axis by having a larger diameter than the width of the narrowed portion (or neck 225) of the suture slot 226.

FIGS. 35a-35d show another needle distal section 230 and inner member 232 in a retracted configuration. The embodiment shown in FIGS. 35a-35d differs from that shown above in that the embodiment shown in FIGS. 35a-35d includes a cleat type constraining feature 234. Cleat 234 includes an abutment surface or lip which snugly holds the distal end of the inner member when the inner member is retracted.

Figure 36A:
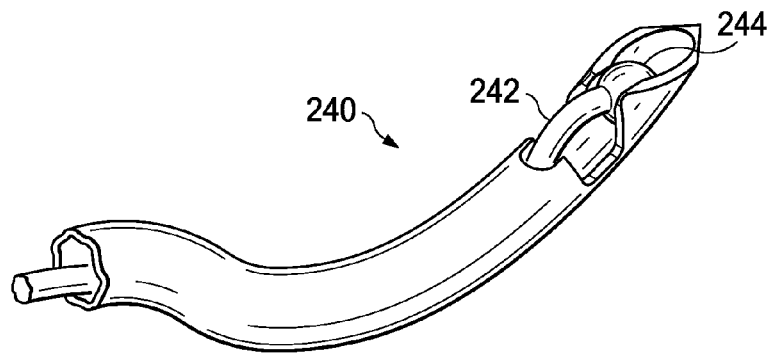
FIG. 36a is a perspective view of the working end of another needle distal section and inner member shown in a retracted configuration.
Figure 36B:
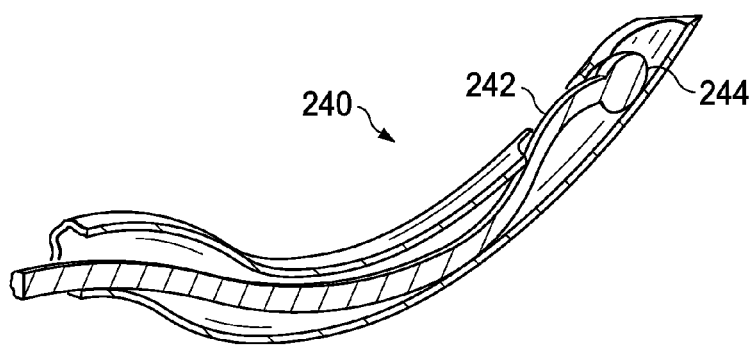
Figure 36C:
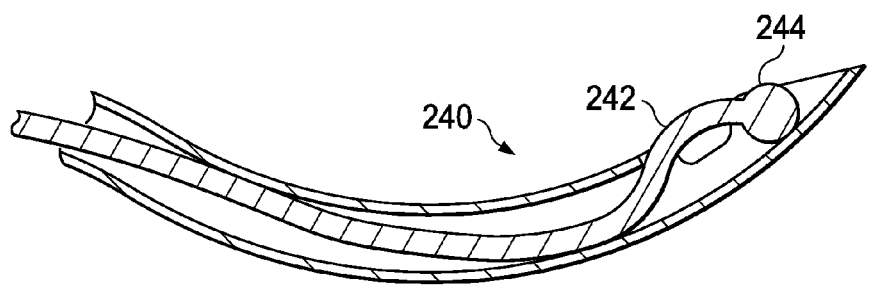

FIGS. 36a-36c show another needle distal section 240 and inner member 242 in a retracted configuration. The embodiment shown in FIGS. 36a-36c differs from that shown above in that the embodiment shown in FIGS. 36a-36c includes a bulbous constraining feature 244. In particular, the inner member 242 terminates in a rounded spherical shape 244. The bulb snugly fits within the needle slot (e.g., by interference fit). Bulb 244 may be bonded or otherwise affixed to inner member, or may be formed as part of the inner member.

The above described constraining features serve to further or redundantly secure inner member within the slot to prevent deployment of the inner member, and to prevent inadvertent release of the suture.

Other modifications and variations can be made to the disclosed embodiments without departing from the subject invention. For example, other methods for suture manipulation and tissue repair will be apparent to the skilled artisan. Moreover, the instruments and methods described herein may be utilized in other regions of the body (e.g., knee, hip, etc.) and for other tissue treatment procedures. Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. A suture instrument for manipulating and passing suture through a tissue, said instrument comprising:
    a handle;
    an elongate tubular shaft extending from the handle, the tubular shaft comprising a distal section including a tapered outer diameter;
    a needle extending from the distal section of the tubular shaft, the needle comprising an outer body defining a lumen extending therethrough, the lumen truncated by a beveled end defining an open and beveled distal terminus of the needle, the lumen extending through the beveled end; and wherein a laterally disposed slot extends from the beveled end and along the body, the slot having an single cutoff and a proximal shoulder the proximal shoulder defining a proximal most edge of the slot so that the lumen extending proximally from the proximal shoulder is completely enclosed; and
    an elongate inner member configured to slide axially along said lumen of said needle so as to move a distal section of said inner member between a retracted configuration in which at least a portion of the inner member distal section is situated within the slot of the needle, and an extended configuration in which the distal section extends from the slot of the needle; and wherein the distal section of the inner member has a preformed shape which the inner member distal section assumes when the inner member is in the extended configuration and the inner member distal section is unconstrained by the lumen of the needle, said preformed shape comprising a first bend which directs the distal section of the inner member at a first angle laterally away from a needle axis, said needle axis extending through the needle towards the distal terminus of the needle;
    and wherein the inner member distal section comprises a tooth or hook proximal a distal end of the inner member; wherein the inner member distal section defines a first length having a first cross-section adjacent the first bend and a second length distal to the first bend having a second cross-section, greater than the first cross-section; and wherein the distal section of the inner member, the tooth or hook and the slot of the needle cooperate together to clamp a suture disposed therebetween when the inner member is in the retracted configuration.

2. The suture instrument of claim 1 wherein the inner member is branchless.

3. The suture instrument of claim 1 wherein the body of the needle comprises a side wall, and a suture holding section in the side wall for locating the suture when clamped between the needle and the inner member.

4. The suture instrument of claim 3 wherein the suture holding section comprises a recess in the side wall, the recess comprising a proximal and distal surface, wherein both surfaces are oriented at a non-zero angle relative to a longitudinal axis of the needle and spaced proximally from the needle distal terminus.

5. The suture instrument of claim 4 wherein the recess distal surface, and inner member distal section are configured so as to render an axial gap therebetween when in the retracted configuration, so as to allow the suture to slide.

6. The suture instrument of claim 5 wherein the distal surface forms a distal ramp and said distal ramp forms an angle between 20 and 65 degrees with the needle axis.

7. The suture instrument of claim 4 wherein the recess proximal surface defines a proximal ramp at an angle greater than or equal to 90 degrees with the needle axis.

8. The suture instrument of claim 3 wherein the slot further comprises a wire relief section proximal the suture holding section.

9. The suture instrument of claim 1 wherein the first angle of the inner member is up to 90 degrees when unconstrained.

10. The suture instrument of claim 9 wherein the inner member comprises a discrete second bend distal to the first bend.

11. The suture instrument of claim 10 wherein the second bend directs a length of the distal section of the inner member at a second angle with the needle axis, said second angle less than the first angle.

12. The suture instrument of claim 10 wherein the inner member comprises a discrete third bend distal to the second bend.

13. The suture instrument of claim 1 wherein the inner member comprises a wire bundle.

14. The suture instrument of claim 1 further comprising a lever movably disposed in said handle and linked to the inner member to manipulate the inner member from the retracted configuration to the extended configuration.

15. The suture instrument of claim 1 wherein the shape of a distal section of the needle is curved.

16. The suture instrument of claim 15 wherein the shape of the distal section of the needle is crescent shaped.

17. The suture instrument of claim 1 wherein the tooth is disposed on a side of the inner member facing the slot.

18. The suture instrument of claim 1 wherein the beveled end comprises a single oblique angle across the entire distal terminus of the needle.

19. The suture instrument of claim 1 wherein an outer surface of the needle is configured so as to form a needle point on a distal circumferential edge of the beveled end, configured to penetrate tissue.

20. The suture instrument of claim 1 wherein the first length has a first longitudinal axis, and the second length has a second longitudinal axis, and wherein the first and second longitudinal axes are axially continuous.

21. A suture instrument for manipulating and passing suture through a tissue, said instrument comprising:
a handle;
a first elongate tubular shaft having a first diameter extending from the handle and a second elongate tubular shaft extending from the first tubular shaft having a second diameter smaller than the first diameter, the second tubular shaft comprising a distal section;
a needle having a third diameter smaller than the first and second diameter extending from the distal section of the tubular shaft, the needle comprising an outerbody defining a lumen extending therethrough the needle terminating with a distal beveled end with the lumen extending therethrough, and a second beveled portion on an outer surface of the needle configured to form a point on a distal most edge of the needle, and wherein the needle further comprises a slot extending proximally from the beveled end and along the body and in communication with said lumen;
an elongate inner member axially moveable within said lumen and relative to said slot of said needle, said inner member having a first length defining a first diameter adjacent the first bend and a second length distal to the first bend having a second diameter, greater than the first diameter, said inner member and needle cooperating together to move between a plurality of configurations, said plurality of configurations comprising:
i) a closed configuration in which at least a portion of a distal section of the inner member is situated within the slot of the needle to clamp the suture therebetween;
ii) an open configuration in which the distal section of the inner member extends from the slot of the needle and defines a suture capture zone between the inner member and the needle; and
iii) an intermediate configuration in which the inner member and the needle loosely encircle a section of suture such that the suture is slidably held therebetween.

22. The suture instrument of claim 21 wherein the distal section of the inner member has a preformed shape which the inner member assumes when the inner member is in the open configuration.

23. The suture instrument of claim 22 wherein the inner member preformed shape comprises a plurality of discrete bends.

24. The suture instrument of claim 23 wherein the inner member comprises a first proximal bend which directs the inner member distal section laterally away from the needle at an angle up to 90 degrees relative to a needle axis when in the open configuration.

25. The suture instrument of claim 24 wherein the inner member further comprises a discrete second bend distal to the first bend and a discrete third bend distal to both the first and second bend, the third bend angled so as to direct an inner member distal tip towards the slot, the second and third bend separated by an approximately straight portion of the inner member.

26. The suture instrument of claim 25 wherein when the inner member is in the closed configuration, the inner member straight portion is disposed substantially outside of the needle slot, coaxial with a needle axis and the inner member distal tip is disposed within the lumen.

27. The suture instrument of claim 21 wherein the needle comprises a crescent shape.

28. The suture instrument of claim 21 wherein the slot comprises a plurality of sections, and said plurality of sections including a proximally disposed wire relief section, and a suture holding section distal to the wire relief section.

29. The suture instrument of claim 21 wherein the slot further comprises a recess having a distal and proximal ramped surface axially spaced away from each other, and in the intermediate configuration, the distal ramped surface and inner member distal section are configured to render a gap between the suture, distal ramped surface and inner member distal section sufficient to allow the suture to slide.

30. The suture instrument of claim 1 or 21 wherein the inner member terminates with a ferrule-type or bulbous end.

* * * * *